US009523701B2

(12) United States Patent
Bunce et al.

(10) Patent No.: US 9,523,701 B2
(45) Date of Patent: *Dec. 20, 2016

(54) SAMPLE PLATE SYSTEMS AND METHODS

(75) Inventors: Adrian Bunce, Worthing (GB); Andrew Fusellier, Guernsey (GB)

(73) Assignee: DYNEX TECHNOLOGIES, INC., Chantilly, VA (US)

(*) Notice: Subject to any disclaimer, the term of this patent is extended or adjusted under 35 U.S.C. 154(b) by 1415 days.

This patent is subject to a terminal disclaimer.

(21) Appl. No.: 13/187,791

(22) Filed: Jul. 21, 2011

(65) Prior Publication Data

US 2012/0183977 A1 Jul. 19, 2012

Related U.S. Application Data

(63) Continuation-in-part of application No. 12/846,580, filed on Jul. 29, 2010, now Pat. No. 8,541,246.

(30) Foreign Application Priority Data

| Jul. 29, 2009 | (GB) | 0913258.0 |
| Oct. 7, 2009 | (GB) | 0917555.5 |
| Apr. 13, 2010 | (GB) | 1006087.9 |
| Jan. 25, 2011 | (GB) | 1101222.6 |
| Apr. 19, 2011 | (GB) | 1106618.0 |

(51) Int. Cl.
| *G01N 33/543* | (2006.01) |
| *G01N 35/10* | (2006.01) |
| *B01L 3/00* | (2006.01) |
| *G01N 35/00* | (2006.01) |

(52) U.S. Cl.
CPC ......... *G01N 35/1081* (2013.01); *B01L 3/5085* (2013.01); *G01N 33/54366* (2013.01); *B01J 2219/005* (2013.01); *B01J 2219/00317* (2013.01); *B01J 2219/00459* (2013.01); *B01J 2219/00468* (2013.01); *B01J 2219/00662* (2013.01); *B01L 2200/0668* (2013.01); *B01L 2300/0829* (2013.01); *G01N 2035/00574* (2013.01); *G01N 2035/1086* (2013.01)

(58) Field of Classification Search
None
See application file for complete search history.

(56) References Cited

U.S. PATENT DOCUMENTS

| 2,956,931 A | 10/1960 | Goldberg |
| 4,200,110 A | 4/1980 | Peterson et al. |
| 4,415,098 A | 11/1983 | Haas |
| 4,469,863 A | 9/1984 | Ts'o et al. |
| 4,499,052 A | 2/1985 | Fulwyler |
| 4,591,556 A | 5/1986 | Saxholm |
| 4,681,742 A | 7/1987 | Johnson et al. |
| 4,682,895 A | 7/1987 | Costello |
| 4,785,814 A | 11/1988 | Kane |
| 4,797,259 A | 1/1989 | Matkovich et al. |
| 4,822,746 A | 4/1989 | Walt |
| 4,824,789 A | 4/1989 | Yafuso et al. |
| 4,999,306 A | 3/1991 | Yafuso et al. |
| 5,002,867 A | 3/1991 | Macevicz |
| 5,028,545 A | 7/1991 | Soini |
| 5,034,506 A | 7/1991 | Summerton et al. |
| 5,105,305 A | 4/1992 | Betzig et al. |
| 5,114,864 A | 5/1992 | Walt |
| 5,132,242 A | 7/1992 | Cheung |
| 5,143,853 A | 9/1992 | Walt |
| 5,176,881 A | 1/1993 | Sepaniak et al. |
| 5,188,965 A | 2/1993 | Wannlund |
| 5,194,300 A | 3/1993 | Cheung |
| 5,216,141 A | 6/1993 | Benner |
| 5,235,033 A | 8/1993 | Summerton et al. |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,254,311 A | 10/1993 | Ushikubo |
| 5,254,477 A | 10/1993 | Walt |
| 5,270,163 A | 12/1993 | Gold et al. |
| 5,298,741 A | 3/1994 | Walt et al. |
| 5,302,509 A | 4/1994 | Cheeseman |
| 5,310,523 A | 5/1994 | Smethers et al. |
| 5,320,814 A | 6/1994 | Walt et al. |
| 5,357,590 A | 10/1994 | Auracher |
| 5,380,489 A | 1/1995 | Sutton et al. |

(Continued)

FOREIGN PATENT DOCUMENTS

| AU | 775056 B2 | 7/2004 |
| CA | 2170249 A1 | 3/1995 |
| CN | 1399132 | 2/2003 |
| CN | 1448719 | 10/2003 |
| CN | 1448723 | 10/2003 |
| CN | 1687781 | 10/2005 |
| CN | 201096781 | 8/2008 |
| CN | 101334409 | 12/2008 |
| EP | 154687 | 9/1985 |
| EP | 0087899 B1 | 12/1986 |

(Continued)

OTHER PUBLICATIONS

Dunbar et al. Customized Probe and Primer Design for SNP Detection: Development of FlexMAP™ Microsphere-Based Assays on the Luminex® Platform Using DNASIS® MAX Software. Technical Bulletin presented at PharmaDiscovery, May 10-12, Washington, DC, 2005.

(Continued)

*Primary Examiner* — Ann Lam
(74) *Attorney, Agent, or Firm* — Diederiks & Whitelaw, PLC

(57) ABSTRACT

A sample plate comprising a sample well is disclosed. The sample well can comprise one or more bead retaining chambers. A method of using the sample plate and a kit comprising the sample plate is also disclosed.

44 Claims, 20 Drawing Sheets

(56) References Cited

U.S. PATENT DOCUMENTS

| | | |
|---|---|---|
| 5,382,512 A | 1/1995 | Smethers et al. |
| 5,386,023 A | 1/1995 | Sanghvi et al. |
| 5,435,724 A | 7/1995 | Goodman et al. |
| 5,475,096 A | 12/1995 | Gold et al. |
| 5,481,629 A | 1/1996 | Tabuchi |
| 5,494,798 A | 2/1996 | Gerdt et al. |
| 5,496,997 A | 3/1996 | Pope |
| 5,512,490 A | 4/1996 | Walt et al. |
| 5,516,635 A | 5/1996 | Ekins et al. |
| 5,518,883 A | 5/1996 | Soini |
| 5,545,531 A | 8/1996 | Rava et al. |
| 5,565,324 A | 10/1996 | Still et al. |
| 5,567,588 A | 10/1996 | Gold et al. |
| 5,573,909 A | 11/1996 | Singer et al. |
| 5,575,849 A | 11/1996 | Honda et al. |
| 5,580,735 A | 12/1996 | Malick et al. |
| 5,595,877 A | 1/1997 | Gold et al. |
| 5,602,240 A | 2/1997 | De Mesmaeker et al. |
| 5,620,853 A | 4/1997 | Smethers et al. |
| 5,633,972 A | 5/1997 | Walt et al. |
| 5,637,459 A | 6/1997 | Burke et al. |
| 5,637,684 A | 6/1997 | Cook et al. |
| 5,639,603 A | 6/1997 | Dower et al. |
| 5,644,048 A | 7/1997 | Yau |
| 5,649,576 A | 7/1997 | Kirk et al. |
| 5,656,241 A | 8/1997 | Seifert et al. |
| 5,674,698 A | 10/1997 | Zarling et al. |
| 5,683,867 A | 11/1997 | Biesecker et al. |
| 5,690,894 A | 11/1997 | Pinkel et al. |
| 5,705,337 A | 1/1998 | Gold et al. |
| 5,719,063 A | 2/1998 | Block |
| 5,770,157 A | 6/1998 | Cargill et al. |
| 5,814,524 A | 9/1998 | Walt et al. |
| 5,837,196 A | 11/1998 | Pinkel et al. |
| 5,840,256 A | 11/1998 | Demers et al. |
| 5,843,666 A | 12/1998 | Akhavan-Tafti et al. |
| 5,854,684 A | 12/1998 | Stabile et al. |
| 5,858,648 A * | 1/1999 | Steel et al. .................. 435/5 |
| 5,863,708 A | 1/1999 | Zanzucchi et al. |
| 5,874,219 A | 2/1999 | Rava et al. |
| 5,885,529 A | 3/1999 | Babson et al. |
| 5,888,723 A | 3/1999 | Sutton et al. |
| 5,900,481 A | 5/1999 | Lough et al. |
| 5,916,526 A | 6/1999 | Robbins |
| 6,023,540 A | 2/2000 | Walt et al. |
| 6,037,186 A | 3/2000 | Stimpson |
| 6,071,748 A | 6/2000 | Modlin et al. |
| 6,074,614 A | 6/2000 | Hafeman et al. |
| 6,083,763 A | 7/2000 | Balch |
| 6,251,691 B1 | 6/2001 | Seul |
| 6,273,128 B1 * | 8/2001 | Paczonay .................. 137/512.3 |
| 6,387,707 B1 | 5/2002 | Seul et al. |
| 6,429,027 B1 | 8/2002 | Chee et al. |
| 6,468,811 B1 | 10/2002 | Seul |
| 6,514,771 B1 | 2/2003 | Seul |
| 6,518,056 B2 | 2/2003 | Schembri et al. |
| 6,602,702 B1 | 8/2003 | McDevitt et al. |
| 6,620,584 B1 | 9/2003 | Chee et al. |
| 6,649,403 B1 | 11/2003 | Mcdevitt et al. |
| 6,680,206 B1 | 1/2004 | McDevitt et al. |
| 6,770,441 B2 | 8/2004 | Dickinson et al. |
| 6,797,524 B1 | 9/2004 | Seul |
| 6,858,394 B1 | 2/2005 | Chee et al. |
| 6,859,570 B2 | 2/2005 | Walt et al. |
| 6,887,431 B1 | 5/2005 | Vann et al. |
| 6,905,885 B2 | 6/2005 | Colston et al. |
| 6,908,770 B1 | 6/2005 | McDevitt et al. |
| 6,916,661 B2 | 7/2005 | Chandler et al. |
| 6,942,968 B1 | 9/2005 | Dickinson et al. |
| 6,955,751 B1 | 10/2005 | Seul |
| 6,958,245 B2 | 10/2005 | Seul et al. |
| 6,962,822 B2 | 11/2005 | Hart et al. |
| 6,964,747 B2 | 11/2005 | Banerjee et al. |
| 6,969,488 B2 | 11/2005 | Bridgham et al. |
| 6,977,722 B2 | 12/2005 | Wohlstadter et al. |
| 6,991,941 B1 | 1/2006 | Seul |
| 6,998,274 B2 | 2/2006 | Chee et al. |
| 7,001,589 B2 | 2/2006 | Mondain-Monval et al. |
| 7,011,955 B1 | 3/2006 | Stemmler et al. |
| 7,022,517 B1 | 4/2006 | McDevitt et al. |
| 7,033,754 B2 | 4/2006 | Chee et al. |
| 7,033,821 B2 | 4/2006 | Kim et al. |
| 7,041,453 B2 | 5/2006 | Yang |
| 7,041,510 B2 | 5/2006 | Seul et al. |
| 7,049,077 B2 | 5/2006 | Yang |
| 7,056,746 B2 | 6/2006 | Seul et al. |
| 7,057,704 B2 | 6/2006 | Seul et al. |
| 7,060,431 B2 | 6/2006 | Chee et al. |
| 7,083,914 B2 | 8/2006 | Seul et al. |
| 7,090,759 B1 | 8/2006 | Seul |
| 7,101,510 B2 | 9/2006 | Vann et al. |
| 7,118,900 B2 | 10/2006 | Seul et al. |
| 7,144,119 B2 | 12/2006 | Seul et al. |
| 7,156,315 B2 | 1/2007 | Seul et al. |
| 7,157,228 B2 | 1/2007 | Hashmi et al. |
| 7,166,431 B2 | 1/2007 | Chee et al. |
| 7,195,913 B2 | 3/2007 | Guire et al. |
| 7,202,038 B2 | 4/2007 | Seul |
| 7,211,183 B2 | 5/2007 | Seul et al. |
| 7,219,800 B2 | 5/2007 | Bülow |
| 7,226,734 B2 | 6/2007 | Chee et al. |
| 7,255,895 B2 | 8/2007 | Banerjee et al. |
| 7,282,370 B2 | 10/2007 | Bridgham et al. |
| 7,285,384 B2 | 10/2007 | Fan et al. |
| 7,291,504 B2 | 11/2007 | Seul |
| 7,306,918 B2 | 12/2007 | Hashmi et al. |
| 7,314,718 B1 | 1/2008 | Dasgupta et al. |
| 7,315,637 B2 | 1/2008 | Xi et al. |
| 7,320,864 B2 | 1/2008 | Yang |
| 7,332,349 B2 | 2/2008 | Yang et al. |
| 7,335,153 B2 | 2/2008 | Seul et al. |
| 7,344,841 B2 | 3/2008 | Hashmi et al. |
| 7,347,975 B2 | 3/2008 | Vann et al. |
| 7,361,309 B2 | 4/2008 | Vann et al. |
| 7,371,325 B2 | 5/2008 | Kane |
| 7,384,606 B2 | 6/2008 | Vann et al. |
| 7,390,676 B2 | 6/2008 | Seul et al. |
| 7,427,512 B2 | 9/2008 | Seul |
| 7,465,540 B2 | 12/2008 | Jacobson et al. |
| 7,498,054 B2 | 3/2009 | Banerjee et al. |
| 7,499,806 B2 | 3/2009 | Kermani et al. |
| 7,501,266 B2 | 3/2009 | Hashmi et al. |
| 7,507,588 B2 | 3/2009 | Mehrpouyan et al. |
| 7,526,114 B2 | 4/2009 | Xia et al. |
| 7,563,576 B2 | 7/2009 | Chee et al. |
| 7,574,305 B2 | 8/2009 | Seul et al. |
| 7,588,908 B2 | 9/2009 | Buechler et al. |
| 7,595,279 B2 | 9/2009 | Wang et al. |
| 7,604,718 B2 | 10/2009 | Zhang et al. |
| 7,612,020 B2 | 11/2009 | Stuelpnagel et al. |
| 7,612,193 B2 | 11/2009 | Hashmi et al. |
| 7,618,792 B2 | 11/2009 | Banerjee |
| 7,635,565 B2 | 12/2009 | Hashmi et al. |
| 7,659,983 B2 | 2/2010 | Moon et al. |
| 7,682,788 B2 | 3/2010 | Sigal et al. |
| 7,704,730 B2 | 4/2010 | Stromgren et al. |
| 7,732,575 B2 | 6/2010 | Wang et al. |
| 7,807,448 B2 | 10/2010 | Glezer et al. |
| 7,842,246 B2 | 11/2010 | Wholstadter et al. |
| 7,855,054 B2 | 12/2010 | Schneider et al. |
| 7,932,022 B2 | 4/2011 | Yang |
| 7,981,362 B2 | 7/2011 | Glezer et al. |
| 7,985,579 B2 | 7/2011 | Cecchi |
| 8,114,681 B2 | 2/2012 | Martin et al. |
| 8,287,823 B2 | 10/2012 | Sellers et al. |
| 8,442,689 B2 | 5/2013 | Lovell et al. |
| 8,470,590 B2 | 6/2013 | Adrien et al. |
| 8,486,629 B2 | 7/2013 | Banerjee et al. |
| 8,541,246 B2 * | 9/2013 | Bunce et al. .................. 436/518 |
| 8,658,388 B2 | 2/2014 | Harvey et al. |
| 8,877,141 B2 * | 11/2014 | Yu .................. B01L 3/5025 422/407 |
| 9,244,069 B2 * | 1/2016 | Bunce .................. 436/518 |
| 2002/0042045 A1 * | 4/2002 | Lee et al. .................. 435/5 |

(56) References Cited

U.S. PATENT DOCUMENTS

| | | |
|---|---|---|
| 2003/0008410 A1 | 1/2003 | Hechinger |
| 2003/0091475 A1 | 5/2003 | Yu et al. |
| 2003/0143580 A1 | 7/2003 | Straus |
| 2003/0186228 A1 | 10/2003 | McDevitt et al. |
| 2004/0076948 A1 | 4/2004 | Pettersson |
| 2004/0185482 A1 | 9/2004 | Stuelpnagel et al. |
| 2004/0241748 A1 | 12/2004 | Ault-Riche et al. |
| 2004/0241776 A1 | 12/2004 | Geister et al. |
| 2005/0064209 A1 | 3/2005 | Haines et al. |
| 2005/0079621 A1 | 4/2005 | Elmes et al. |
| 2005/0130318 A1 | 6/2005 | Vann et al. |
| 2005/0202447 A1 | 9/2005 | Opperman et al. |
| 2005/0244838 A1 | 11/2005 | Wojtowicz |
| 2005/0244870 A1 | 11/2005 | Chee et al. |
| 2005/0255491 A1 | 11/2005 | Lee et al. |
| 2006/0012130 A1 | 1/2006 | Vann et al. |
| 2006/0063197 A1 | 3/2006 | Anderson et al. |
| 2006/0073072 A1 | 4/2006 | Rudloff |
| 2006/0188943 A1 | 8/2006 | Seul et al. |
| 2006/0252044 A1 | 11/2006 | Okumura et al. |
| 2006/0272738 A1 | 12/2006 | Lim et al. |
| 2006/0275178 A1 | 12/2006 | Chang et al. |
| 2007/0003954 A1 | 1/2007 | Kodadek |
| 2007/0053800 A1* | 3/2007 | Lehto ............... 422/102 |
| 2007/0154970 A1 | 7/2007 | Buechler et al. |
| 2007/0207513 A1 | 9/2007 | Sorensen et al. |
| 2007/0231824 A1 | 10/2007 | Chee et al. |
| 2007/0259366 A1 | 11/2007 | Lawrence et al. |
| 2008/0039343 A1 | 2/2008 | Guire et al. |
| 2008/0050769 A1 | 2/2008 | Huang et al. |
| 2008/0124769 A1 | 5/2008 | Paek et al. |
| 2008/0182248 A1 | 7/2008 | Fan et al. |
| 2008/0220982 A1 | 9/2008 | Vu |
| 2008/0303870 A1 | 12/2008 | Verbeek et al. |
| 2008/0305969 A1 | 12/2008 | Dijksman et al. |
| 2009/0025489 A1* | 1/2009 | Christensen et al. ......... 73/864 |
| 2009/0033690 A1 | 2/2009 | Pierik et al. |
| 2009/0042734 A1 | 2/2009 | Yoshida et al. |
| 2009/0068680 A1 | 3/2009 | Mapes et al. |
| 2009/0069200 A1 | 3/2009 | Yu |
| 2009/0123336 A1 | 5/2009 | Yang et al. |
| 2009/0156426 A1 | 6/2009 | Schiestel et al. |
| 2009/0163378 A1 | 6/2009 | Mehrpouyan et al. |
| 2009/0217990 A1* | 9/2009 | Kim et al. .................. 137/539 |
| 2009/0270278 A1 | 10/2009 | Lim et al. |
| 2009/0298716 A1 | 12/2009 | Stuelpnagel et al. |
| 2010/0035243 A1 | 2/2010 | Muller et al. |
| 2010/0047845 A1 | 2/2010 | Woodside et al. |
| 2010/0075865 A1 | 3/2010 | Trau et al. |
| 2011/0027914 A1 | 2/2011 | Bunce et al. |
| 2011/0223690 A1 | 9/2011 | Raj |
| 2011/0232125 A1 | 9/2011 | Lea |
| 2011/0263463 A1 | 10/2011 | Rothberg et al. |
| 2012/0135876 A1 | 5/2012 | Rozhok et al. |
| 2013/0034284 A1 | 2/2013 | Honkanen et al. |
| 2013/0071915 A1 | 3/2013 | Bustillo et al. |
| 2013/0266969 A1 | 10/2013 | Honkanen et al. |

FOREIGN PATENT DOCUMENTS

| | | |
|---|---|---|
| EP | 302673 | 2/1989 |
| EP | 0715719 B1 | 4/2000 |
| EP | 1171230 B1 | 11/2002 |
| EP | 1141712 B1 | 7/2005 |
| EP | 1153303 B1 | 9/2006 |
| EP | 1434055 B1 | 9/2006 |
| EP | 1722236 A1 | 11/2006 |
| EP | 2045601 A1 | 4/2009 |
| EP | 1593967 B1 | 7/2009 |
| EP | 2397224 | 12/2011 |
| JP | 1274066 | 11/1989 |
| JP | 10332593 | 12/1998 |
| JP | 2000-346842 A | 12/2000 |
| JP | 2003329696 | 11/2003 |
| JP | 2007-285828 A | 11/2007 |
| JP | 2009-195160 A | 9/2009 |
| RU | 2262939 C2 | 10/2005 |
| RU | 2284035 C2 | 9/2006 |
| SU | 1530242 A1 | 12/1989 |
| WO | WO 88/07679 | 10/1988 |
| WO | WO 92/01513 A1 | 2/1992 |
| WO | WO 93/06121 | 4/1993 |
| WO | WO 97/40385 | 10/1997 |
| WO | WO 98/40726 | 9/1998 |
| WO | WO 98/50782 | 11/1998 |
| WO | WO 00/48000 | 8/2000 |
| WO | WO 01/58482 A1 | 8/2001 |
| WO | WO 02/30561 A2 | 4/2002 |
| WO | WO 02/30561 A3 | 5/2003 |
| WO | WO 03/036263 A2 | 5/2003 |
| WO | WO 03/036263 A3 | 10/2003 |
| WO | WO 03/081253 | 10/2003 |
| WO | WO 03/089139 | 10/2003 |
| WO | WO 2004/111260 A2 | 12/2004 |
| WO | WO 2004/111260 A3 | 11/2005 |
| WO | WO 2005/119201 | 12/2005 |
| WO | WO 2006/090180 | 8/2006 |
| WO | WO 2006/102321 A2 | 9/2006 |
| WO | WO 2007/042972 | 4/2007 |
| WO | WO 2007/067680 A2 | 6/2007 |
| WO | WO 2007/067680 A3 | 8/2007 |
| WO | WO 2006/102321 A3 | 9/2007 |
| WO | WO 2009/029561 A2 | 3/2009 |
| WO | WO 2009/029561 A3 | 5/2009 |
| WO | WO 2010/008519 A2 | 1/2010 |
| WO | WO 2010/025190 | 3/2010 |
| WO | WO 2010/029175 | 3/2010 |
| WO | WO 2010/008519 A3 | 5/2010 |
| WO | WO 2011/035177 | 3/2011 |
| WO | WO 2012/013959 | 2/2012 |
| WO | WO 2013/074643 | 5/2013 |

OTHER PUBLICATIONS

European search report dated Nov. 10, 2011 for Application No. 10275038.7.

International search report dated Jan. 4, 2011 for PCT/US2010/001443.

Miller et al. Basic concepts of microarrays and potential applications in clinical microbiology. Clin Microbiol Rev 2294:611-633, 2009.

Notice of invitation to pay additional fees dated Nov. 5, 2011 for PCT application No. GB2010/001443.

Office action and search report dated Nov. 24, 2009 for Application No. GB 0913258.0.

Office action dated Jul. 28, 2011 for Application No. GB 1006087.9.

Office action dated Jul. 9, 2012 for U.S. Appl. No. 12/846,580.

U.S. Appl. No. 13/463,507, filed May 3, 2012, Bunce et al.

European office action dated Sep. 15, 2011 for Application No. 10275038.7.

International search report and written opinion dated Sep. 16, 2011 for PCT/GB2011/051383.

* cited by examiner

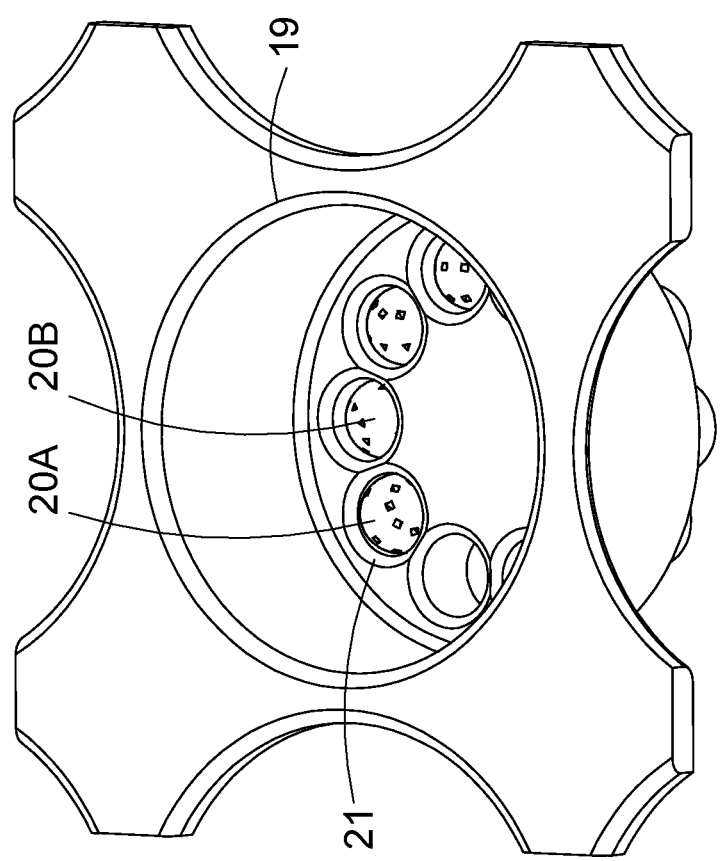

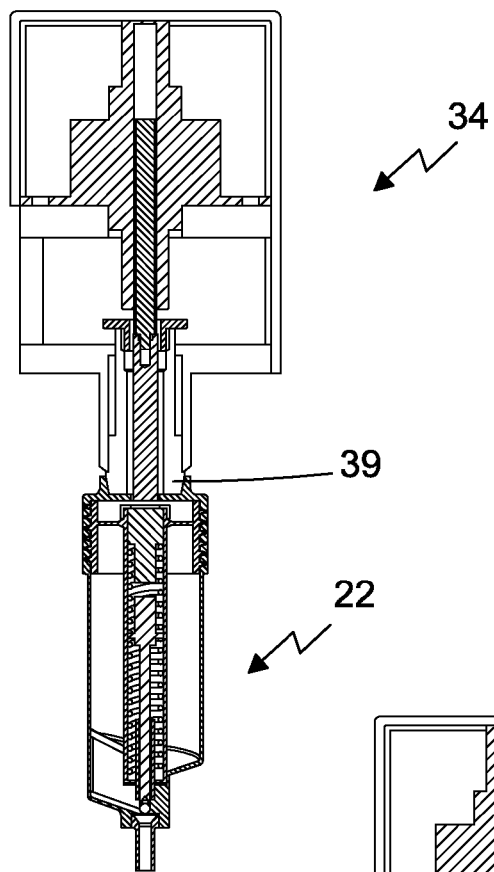
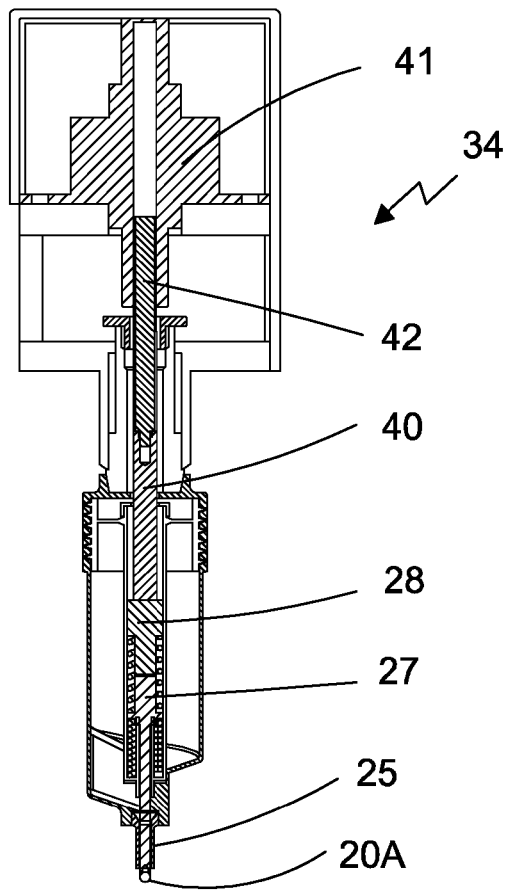
Fig. 7A
Fig. 7B

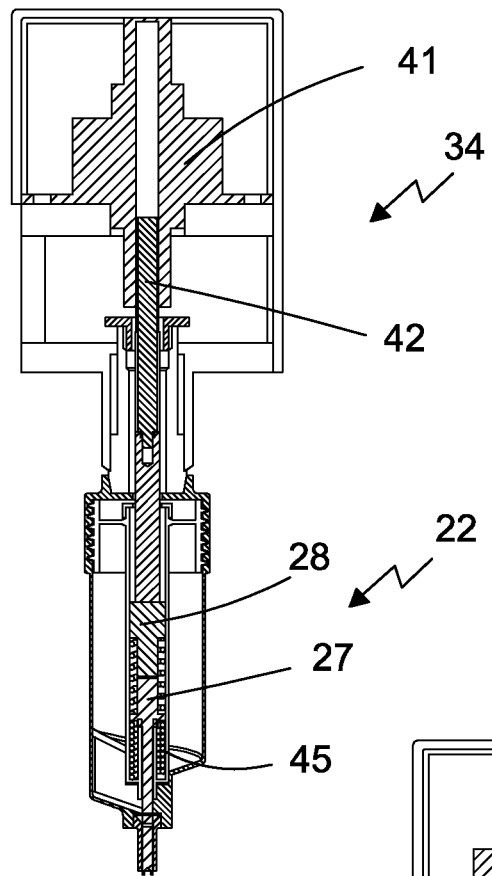
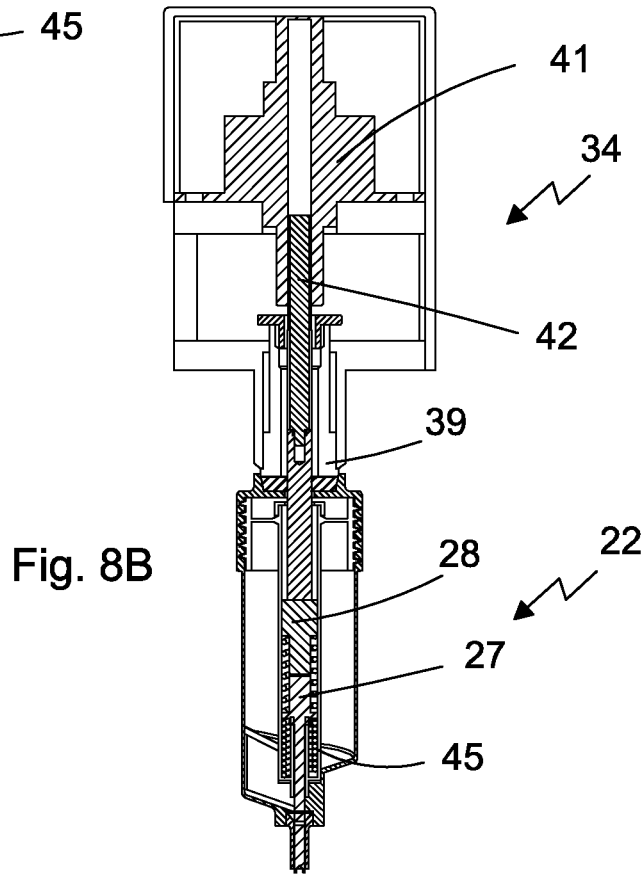
Fig. 8A
Fig. 8B

SAMPLE PLATE SYSTEMS AND METHODS

CROSS-REFERENCE TO RELATED APPLICATIONS

This application claims the benefit of United Kingdom Patent Application Nos. GB 1101222.6, filed on Jan. 25, 2011 and GB 1106618.0, filed on Apr. 19, 2011, each of which is incorporated herein by reference in its entirety. This application is a continuation-in-part application of U.S. Ser. No. 12/846,580, filed on Jul. 29, 2010, which claims priority to United Kingdom Patent Application Nos. GB 0913258.0, filed on Jul. 29, 2009; GB 0917555.5 filed on Oct. 7, 2009; and GB 1006087.9 filed on Apr. 13, 2010, each of which is incorporated herein by reference in its entirety. This application is also related to PCT Patent Application No. PCT/GB2010/001443, filed on Jul. 29, 2010, which is incorporated herein by reference in its entirety.

BACKGROUND

The present invention relates to a sample plate, an automated apparatus, a reagent bead or microsphere dispenser, a method of dispensing reagent beads or microspheres, a kit for performing Enzyme Linked Immunosorbent Assay procedures, a kit for performing nucleic acid probe procedures, a method of manufacturing a sample plate and a computer program executable by the control system of an automated apparatus.

An automated reagent bead or microsphere dispenser for dispensing reagent beads or microspheres into a sample plate is disclosed. The sample plate may be used to carry out diagnostic testing such as Enzyme Linked Immunosorbent Assay ("ELISA") procedures or other immunoassay procedures. Alternatively, the sample plate may be used to carry out testing for DNA or RNA sequences.

In one embodiment, immunoassay procedures are used to test biological products. These procedures can exploit the ability of antibodies produced by the body to recognize and combine with specific antigens which may, for example, be associated with foreign bodies such as bacteria or viruses, or with other body products such as hormones. Once a specific antigen-antibody combination has occurred it can be detected using chromogenic, fluorescent or chemiluminescent materials or less preferably by using radioactive substances. Radioactive substances are less preferred due to environmental and safety concerns regarding their handling, storage and disposal. The same principles can be used to detect or determine any materials which can form specific binding pairs, for example using lectins, rheumatoid factor, protein A or nucleic acids as one of the binding partners.

In one embodiment, ELISA is a form of immunoassay procedure used, wherein one member of the binding pair is linked to an insoluble carrier surface ("the solid phase") such as a sample vessel, and after reaction the bound pair is detected by use of a further specific binding agent conjugated to an enzyme ("the conjugate"). The characteristics and choice of solid phases for capture assays, on methods and reagents for coating solid phases with capture components, on the nature and choice of labels, and on methods for labeling components is well known in the arts and may also be applied to assays for other specific binding pairs. An example of a standard textbook is "ELISA and Other Solid Phase Immunoassays, Theoretical and Practical Aspects", Editors D. M. Kemeny & S. J. Challacombe, published by John Wiley, 1988. Such advice.

In one embodiment of ELISA, the solid phase is coated with a member of the binding pair. An aliquot of the specimen to be examined can incubated with the solid coated solid phase and any analyte that may be present is captured onto the solid phase. After washing to remove residual specimen and any interfering materials it may contain, a second binding agent, specific for the analyte and conjugated to an enzyme can be added to the solid phase. During a second incubation any analyte captured onto the solid phase can combine with the conjugate. After a second washing to remove any unbound conjugate, a chromogenic substrate for the enzyme can be added to the solid phase. Any enzyme present can begin converting the substrate to a chromophoric product. After a specified time the amount of product formed may be measured using a spectrophotometer, either directly or after stopping the reaction.

Many variants are known in the art including fluorogenic and luminogenic substrates for ELISA, direct labeling of the second member of the binding pair with a fluorescent or luminescent molecule (in which case the procedure is not called an ELISA but the process steps are very similar) and nucleic acids or other specific pairing agents instead of antibodies as the binding agent. In some embodiments, the assays use fluid samples, e.g. blood, serum, urine, etc., which are aspirated from a sample tube and are then dispensed into a solid phase. Samples may be diluted prior to being dispensed into the solid phase or they may be dispensed into deep well microplates, diluted in situ and then the diluted analyte may be transferred to the functional solid phase.

In one embodiment, the solid phase is a standard sample vessel known as a microplate, which can be stored easily and which may be used with a variety of biological specimens. The microplate can be made from materials including, but not limited to polystyrene, PVC, Perspex or Lucite. In one embodiment, the microplate measures approximately 5 inches (12.7 cm) in length, 3.3 inches (8.5 cm) in width, and 0.55 inches (1.4 cm) in depth. In one embodiment, the microplate is made from polystyrene wherein the polystyrene's enhanced optical clarity assists visual interpretation of the results of a reaction. The polystyrene microplate can also be compact, lightweight and easily washable. In one embodiment, the microplate is sold under the name "MICROTITRE"®. The microplate can comprise 96 wells (also known as "microwells") which can be symmetrically arranged in an 8×12 array. The microwells can have a maximum volume capacity of approximately 350 µl. In one embodiment, approximately 10-200 µl of fluid is dispensed into a microwell. In some arrangements of the microplate the microwells may be arranged in strips of 8 or 12 wells that can be moved and combined in a carrier to give a complete plate having conventional dimensions.

Positive and negative controls can be supplied with microplates, such as with commercial kits, and are used for quality control and to provide a relative cut-off. After reading the processed microplate, the results of the controls can be checked against the manufacturer's validated values to ensure that the analysis has operated correctly and then the value is used to distinguish positive from negative specimens and a cut off value is calculated. Standards can be provided for quantitative assays and used to build a standard curve from which the concentration of analyte in a specimen may be interpolated.

In one embodiment, the ELISA procedure can involve multiple steps including, but not limited to, one or more of the following: pipetting, incubation, washing, transferring microplates between activities, reading and data analysis.

One or more of the steps (or "phases") involved in the ELISA procedures such as sample distribution, dilution, incubation at specific temperatures, washing, enzyme conjugate addition, reagent addition, reaction stopping and the analysis of results, can be automated. For example, the pipette mechanism used to aspirate and dispense fluid samples uses disposable tips which are ejected after being used so as to prevent cross-contamination of patients' samples. Multiple instrumental controls can be in place to ensure that appropriate volumes, times, wavelengths and temperatures are employed, data transfer and analysis is fully validated and monitored. Automated immunoassay apparatus for carrying out ELISA procedures can be used in laboratories of e.g. pharmaceutical companies, veterinary and botanical laboratories, hospitals and universities for in-vitro diagnostic applications such as testing for diseases and infection, and for assisting in the production of new vaccines and drugs.

ELISA kits can comprise microplates having microwells which have been coated with a specific antibody (or antigen). For example, in the case of a hepatitis B antigen diagnostic kit, the kit manufacturer will dispense anti-hepatitis B antibodies which have been suspended in a fluid into the microwells of a microplate. The microplate is then incubated for a period of time, during which time the antibodies adhere to the walls of the microwells up to the fluid fill level (typically about half the maximum fluid capacity of the microwell). The microwells are then washed leaving a microplate having microwells whose walls are uniformly covered with anti-hepatitis B antibodies up to the fluid fill level.

A testing laboratory can receive a number of sample tubes containing, for example, body fluid from a number of patients. A specified amount of fluid can be aspirated out of the sample tube using a pipette mechanism and dispensed into one or more microwells of a microplate that has been previously prepared by the manufacturer, such as discussed above. If it is desired to test a patient for a number of different diseases, fluid from the patient is typically dispensed into a number of separate microplates, wherein each microplate may have been coated by its manufacturer with a different binding agent. Each microplate can then be processed separately to detect the presence of a different disease. This can lead to analysis of several different analytes with a multiplicity of microplates and transfer of aliquots of the same specimen to the different microplates, resulting in large numbers of processing steps and incubators and washing stations that can cope with many microplates virtually simultaneously. In automated systems this instruments may have multiple incubators and complex programming to avoid clashes between microplates with different requirements. For manual operation either several technicians may be needed or the throughput of specimens is slow. It is possible to combine strips of differently coated microwells into a single carrier, add aliquots of a single specimen to the different types of well and then perform the ELISA in this combined microplate. Constraints on assay development, however, can make this combination difficult to achieve and can lead to errors of assignment of result, while manufacture of microplates with several different coatings in different microwells can present difficulties of quality control.

Conventional ELISA techniques have typically concentrated upon performing the same single test upon a plurality of patient samples per microplate or in detecting the presence of one or more of a multiplicity of analytes in those patients without distinguishing which of the possible analytes is actually present. For example, it is commonplace to determine in a single microwell whether a patient has antibodies to HIV 1 or HIV 2, or HIV 1 or 2 antigens, without determining which analyte is present and similarly for HCV antibodies and antigens.

However, a new generation of assays are being developed which enable multiplexing to be performed. Multiplexing enables multiple different tests to be performed simultaneously upon the same patient sample.

In one embodiment, multiplexing provides a microplate comprising 96 sample wells wherein an array of different capture antibodies is disposed in each sample well. The array can comprise an array of 20 nL spots each having a diameter of 350 μm. The spots can be arranged with a pitch spacing of 650 μm. Each spot corresponds with a different capture antibody.

Multiplexing enables a greater number of data points and more information per assay to be obtained compared with conventional ELISA techniques wherein each sample plate tests for a single analyte of interest. The ability to be able to combine multiple separate tests into the same assay can lead to considerable time and cost savings. Multiplexing also enables the overall footprint of the automated apparatus to be reduced.

Provided herein is a sample plate and associated automated apparatus which has an improved format and which provides a greater flexibility.

In addition to ELISA procedures, a hybridization probe can be used to test for the presence of DNA or RNA sequences. A hybridization probe typically comprises a fragment of nucleic acid, such as DNA or RNA, which is used to detect the presence of nucleotide sequences which are complementary to the nucleic acid sequence of the probe. The hybridization probe can hybridize to single-stranded nucleic acid (e.g. DNA or RNA) whose base sequence allows pairing due to complementarity between the hybridization probe and the sample being analyzed. The hybridization probe may be tagged or labeled with a molecular marker such as a radioactive or more preferably a fluorescent molecule. The probes are inactive until hybridization at which point there is a conformational change and the molecule complex becomes active and will then fluoresce (which can be detected under UV light) DNA sequences or RNA transcripts which have a moderate to high sequence similarity to the probe are then detected by visualizing the probe under UV light.

It is desired to provide an improved sample plate for retaining reagent beads, as well as related systems and methods.

SUMMARY

Disclosed herein are sample plates comprising one or more sample wells, wherein one or more of the sample wells comprise: (a) a base portion; and (b) one or more recesses provided in the base portion; wherein each of the one or more recesses has a dimension for a bead deposited in the well to be substantially retained or secured within the recess, and the bead forms a substantially fluid-tight circumferential seal with a wall of the base portion which defines the recess. In one embodiment, the one or more recesses comprise a blind recess or an open through hole. In one embodiment, the recess is substantially cylindrical. In one embodiment, an opening to the recess is circular. In one embodiment, the recess is conical and has a first diameter which is greater than a diameter of a bead deposited in the recess and a second diameter which is less than a diameter of the bead deposited in the recess. In one embodiment, the through recess has a taper selected from the group consisting of: (i) <0.5°; (ii) 0.5°; (iii) 0.5-1°; (iv) 1-2°; (v) 2-4°; (vi) 4-6°; (vii) 6-8°; (viii) 8-10°; and (ix) >10°. In one embodiment, the diameter or depth of the recess is selected from the group consisting of: (i) <0.5 mm; (ii) 0.5-1.0 mm; (iii) 1.0-1.5 mm; (iv) 1.5-2.0 mm; (v) 2.0-2.5 mm; (vi) 2.5-3.0 mm; (vii) 3.0-3.5 mm; (viii) 3.5-4.0 mm; (ix) 4.0-4.5 mm; (x) 4.5-5.0 mm; (xi) <5.0 mm; and (xii) >5.0 mm. In one embodiment, in at least one sample well the base portion is segmented into a plurality of segments which are arranged at different heights relative to each other. In one embodiment, in at least one sample well, the sample well further comprises one or more baffles or dividers which separates or divides the base portion into at least a first region and a second region. In one embodiment, the one or more baffles or dividers attenuate or eliminate light reflected off one or more reagent beads located in the first region from impinging upon one or more reagent beads located in the second region. In one embodiment, the one or more recesses comprise a countersunk or enlarged portion for facilitating the insertion of a bead into one or more of the through holes or recesses. In one embodiment, the one or more sample wells comprise between 2 and 22 recesses. In one embodiment, the recesses are arranged circumferentially around a central portion of the sample well. In one embodiment, the central portion comprises a central recess. In one embodiment, the central portion does not comprise a recess. In one embodiment, the plurality of recesses is arranged in a substantially symmetrical or regular manner. In one embodiment, the plurality of recesses is arranged in a substantially asymmetrical or irregular manner. In one embodiment, the plurality of recesses is arranged in a substantially linear manner. In one embodiment, the plurality of recesses is arranged in a substantially curved manner. In one embodiment, the sample plate comprises sample wells arranged in an A×B format, wherein A and B are perpendicular axes, and the number of wells along the A axis can be greater than, less than, or equal to the number of wells along the B axis. In one embodiment, the number of wells along the A axis or B axis is at least 2. In one embodiment, the number of wells along the A axis or B axis is between 2 and 15. In one embodiment, one of the sample wells is connected to another sample well by a frangible region. In one embodiment, the sample plate comprises a base comprising a docking portion for securing the sample plate to a corresponding docking portion of a plate frame holder. In one embodiment, the sample plate of claim further comprises a bead. In one embodiment, the bead is attached to a probe. In one embodiment, the probe is a nucleic acid, antibody, antibody fragment, protein, peptide, aptamer, or chemical compound.

Also disclosed herein are bead dispensing systems comprising: (a) a bead dispenser; (b) a sample plate comprising a sample well, wherein the sample well comprises a base portion, wherein the base portion comprises one or more recesses, wherein each of the one or more recesses has a dimension for a bead deposited in the well to be substantially retained or secured within the recess, and the bead forms a substantially fluid-tight circumferential seal with a wall of the base portion which defines the recess; and (c) a control system configured to control dispensing of the bead from the bead dispenser into the sample plate. In one embodiment, the one or more recesses comprise a blind recess or an open through hole. In one embodiment, the bead dispenser comprises: (i) a syringe body comprising an annular chamber surrounding a longitudinal bore, wherein the annular chamber is configured to channel a reagent bead within the annular chamber towards a chamber provided in the bore; (ii) a plunger provided within the longitudinal bore; and (iii) a barrel or nozzle; wherein the plunger is configured to dispense a bead from the chamber into the barrel or nozzle. In one embodiment, the bead dispenser is configured to dispense a plurality of beads automatically.

Also disclosed herein are methods of dispensing beads comprising: (a) providing a bead dispenser comprising a bead; (b) providing a sample plate comprising a sample well, wherein the sample well comprises a base portion; wherein the base portion comprises one or more recesses, wherein each of the one or more recesses has a dimension for a bead deposited in the well to be substantially retained or secured within the recess, and the bead forms a substantially fluid-tight circumferential seal with a wall of the base portion which defines the recess; and (c) controlling the dispensing of the bead from the bead dispenser into the sample plate. In one embodiment, the one or more recesses comprise a blind recess or an open through hole. In one embodiment, the dispensing is performed automatically.

Also disclosed herein are kits for detecting an analyte comprising: (a) a plurality of beads; and (b) sample plate comprising a sample well, wherein the sample well comprises a base portion; wherein the base portion comprises one or more recesses, wherein each of the one or more recesses has a dimension for a bead deposited in the well to be substantially retained or secured within the recess, and the bead forms a substantially fluid-tight circumferential seal with a wall of the base portion which defines the recess. In one embodiment, the one or more recesses comprise a blind recess or an open through hole. In one embodiment, the plurality of beads comprises one or more probes. In one embodiment, the probe is a nucleic acid, antibody, antibody fragment, protein, peptide, aptamer, or chemical compound.

Also disclosed herein are methods of detecting an analyte comprising: (a) adding a sample to a sample plate comprising a sample well, wherein the sample well comprises a base portion; wherein the base portion comprises one or more recesses, wherein each of the one or more recesses has a dimension for a bead deposited in the well to be substantially retained or secured within the recess, and the bead forms a substantially fluid-tight circumferential seal with a wall of the base portion which defines the recess; and (b) detecting binding of an analyte in the sample with the probe. In one embodiment, the recess comprises a blind recess and an open through hole. In one embodiment, the sample plate comprises a plurality of probes and a plurality of analytes are detected. In one embodiment, a plurality of samples is added to the sample plate.

Also disclosed herein are methods of manufacturing a sample plate comprising: (a) providing a sample plate comprising one or more sample wells each having a base portion; and (b) forming one or more recesses in the one or more base portions, wherein each of the one or more recesses has a dimension for a bead deposited in the well to be substantially retained or secured within the recess, and the bead forms a substantially fluid-tight circumferential seal with a wall of the base portion which defines the recess. In one embodiment, the one or more recesses comprises a blind recess or an open through hole.

According to an aspect of the present invention there is provided a sample plate comprising one or more sample wells, wherein one or more of the sample wells comprise:
a base portion; and
one or more open through holes provided in the base portion;
characterized in that:
a reagent bead or microsphere is substantially retained or secured, in use, within the through hole so as to form a substantially fluid-tight circumferential seal with a wall of the base portion which defines the through hole.

The one or more through holes pass from the bottom of the sample well to the rear or bottom surface of the sample plate. As a result, if a reagent bead is not retained or secured within the open through hole then any fluid in the sample well can leak out of the sample well via the through hole.

According to an aspect of the present invention there is provided a sample plate comprising one or more sample wells, wherein one or more of the sample wells comprise:

a base portion; and one or more recesses provided in the base portion; characterized in that:

a reagent bead or microsphere is substantially retained or secured, in use, within the recess so as to form a substantially fluid-tight circumferential seal with a wall of the base portion which defines the recess.

It should be understood that a circular bead within a hole, bore or recess having a square cross-section will not form a fluid-tight circumferential seal with the wall defining the hole, bore or recess. A fluid-tight circumferential seal should be understood as meaning that a barrier is formed around the entire circumference of the bead and the wall defining the hole, bore or recess.

In some embodiments reagent beads or microspheres are retained or secured within a through hole or a recess formed in the base portion of the sample plate. Each reagent bead or microsphere forms a fluid-tight and/or water-tight and/or air-tight seal about the entire outer diameter or circumference of the reagent bead or microsphere.

Once the reagent bead or microsphere is located within the through hole or recess, then fluid is substantially prevented from being able to pass from one side of the through hole or recess to the other side by the reagent bead or microsphere which forms a tight seal about the entire circumference of the reagent bead or microsphere.

Various different embodiments are contemplated.

In some embodiments, the sample plate comprises one or more recesses, wherein the one or more recesses preferably comprise blind recesses that are closed at one end. A blind recess differs from a through hole in that if a reagent bead is not retained or secured in a blind recess then sample fluid within a sample well will not leak out of the sample well.

In some embodiments, open through holes or recesses provided in the base portion of a sample well can be substantially cylindrical and have a diameter less than a diameter of a reagent bead or microsphere deposited in the through hole or the recess so that the reagent bead or microsphere is retained or secured within the through hole or within the recess by an interference or friction fit.

The open through hole or the recess can, according to another embodiment, be conical and have a first diameter which is greater than a diameter of a reagent bead or microsphere deposited in the through hole or in the recess and a second diameter which is less than a diameter of the reagent bead or microsphere deposited in the through hole or in the recess. In some embodiments, reagent beads or microspheres can be secured within the through hole by the taper.

The first diameter can be distal from a portion of the base portion onto which sample fluid is dispensed, in use, and the second diameter would be proximate to the portion of the base portion onto which sample fluid is dispensed in use.

Alternatively, the first diameter can be proximate to a portion of the base portion onto which sample fluid is dispensed, in use, and the second diameter would be distal from the portion of the base portion onto which sample fluid is dispensed in use.

The through hole or the recess can have a taper selected from the group consisting of: (i) <0.5°; (ii) 0.5°; (iii) 0.5-1°; (iv) 1-2°; (v) 2-4°; (vi) 4-6°; (vii) 6-8°; (viii) 8-10°; and (ix) >10°.

An opening to the through hole or recess is preferably circular.

The through hole or recess preferably has a circular cross-sectional shape or profile. According to an embodiment, the through holes or recesses may have a circular cross-section along at least 5%, 10%, 15%, 20%, 25%, 30%, 35%, 40%, 45%, 50%, 55%, 60%, 65%, 70%, 75%, 80%, 85%, 90%, 95% or 100% of the length or depth of the through hole or recess.

In some embodiments the diameter of the through hole or the recess is selected from the group consisting of: (i) <0.5 mm; (ii) 0.5-1.0 mm; (iii) 1.0-1.5 mm; (iv) 1.5-2.0 mm; (v) 2.0-2.5 mm; (vi) 2.5-3.0 mm; (vii) 3.0-3.5 mm; (viii) 3.5-4.0 mm; (ix) 4.0-4.5 mm; (x) 4.5-5.0 mm; (xi) <5.0 mm; and (xii) >5.0 mm.

In some embodiments, the depth of the through hole or the recess is selected from the group consisting of: (i) <0.5 mm; (ii) 0.5-1.0 mm; (iii) 1.0-1.5 mm; (iv) 1.5-2.0 mm; (v) 2.0-2.5 mm; (vi) 2.5-3.0 mm; (vii) 3.0-3.5 mm; (viii) 3.5-4.0 mm; (ix) 4.0-4.5 mm; (x) 4.5-5.0 mm; (xi) <5.0 mm; and (xii) >5.0 mm.

According to an embodiment in at least one sample well (or in all the sample wells) the base portion preferably comprises a plurality of open through holes and/or a plurality of recesses and wherein at least some (or all) of the plurality of open through holes and/or at least some (or all) of the plurality of recesses are arranged so that there is no direct line of sight between reagent beads retained or secured in adjacent open through holes and/or so that there is no direct line of sight between reagent beads retained or secured in adjacent recesses.

In some embodiments, at least one sample well (or in all the sample wells) the base portion can comprise a plurality of open through holes and/or a plurality of recesses and wherein the base portion is segmented into a plurality of segments which are arranged at different heights relative to each other.

In some embodiments, at least one sample well (or in all the sample wells) the base portion can comprise a plurality of open through holes and/or a plurality of recesses and wherein the sample well further comprises one or more baffles or dividers which preferably separates or divides the base portion into at least a first region and a second region.

The one or more baffles or dividers can be arranged so as: (i) to attenuate or eliminate light reflected off one or more reagent beads located in the first region from impinging upon one or more reagent beads located in the second region; and/or (ii) to attenuate or eliminate light reflected off one or more reagent beads located in the second region from impinging upon one or more reagent beads located in the region.

In some embodiments, one or more open through holes or recesses can comprise a countersunk or enlarged portion for facilitating the insertion of a reagent bead or microsphere into one or more of the through holes or recesses.

The one or more sample wells can comprise a plurality of through holes or recesses, e.g., at least 1, 2, 3, 4, 5, 6, 7, 8, 9, 10, 11, 12, 13, 14, 15, 16, 17, 18, 19, 20 or 21 through holes or recesses which are each arranged and adapted to receive, in use, a reagent bead or microsphere.

The one or more through holes or recesses provided in the base portion can be arranged:

(i) circumferentially around a central portion of the sample well; or (ii) with a plurality of through holes or recesses arranged circumferentially around a central through hole or recess; or (iii) in a substantially close-packed manner; or (iv) in a substantially symmetrical or asymmetrical manner; or (v) in a substantially linear or curved manner; or (vi) in a substantially regular or irregular manner; or (vii) in an array; or (viii) in a circle or two or more concentric circles with no through hole or recess located at the centre of the base portion.

In some embodiments, the sample plate comprises sample wells arranged in an A×B format wherein:

A is selected from the group consisting of: (i) 1; (ii) 2; (iii) 3; (iv) 4; (v) 5; (vi) 6; (vii) 7; (viii) 8; (ix) 9; (x) 10; and (xi) >10; and B is selected from the group consisting of: (i) 1; (ii) 2; (iii) 3; (iv) 4; (v) 5; (vi) 6; (vii) 7; (viii) 8; (ix) 9; (x) 10; and (xi) >10.

One or more of the sample wells can be interconnected to one or more other sample wells by one or more frangible regions or connections so that the sample plate can be separated by a user into a plurality of smaller sample plates, sample strips or individual sample wells.

In some embodiments, the sample plate is an Immunoassay sample plate.

The sample plate can, in some embodiments, comprise a hybridization probe for detecting the presence of complementary DNA or RNA samples.

The sample plate can comprise a base having a female, male or other docking portion for securing the sample plate to a corresponding male, female or other docking portion of a plate frame holder.

Disclosed herein are combinations of a sample plate as described above and one or more reagent beads or microspheres inserted or located in one or more of the through holes or recesses of the one or more sample wells.

At least some or substantially all of the reagent beads or microspheres can carry, comprise or are otherwise coated with a reagent, wherein the reagent is arranged and adapted to assay for an analyte of interest in a sample liquid.

At least some or substantially all of the reagent beads or microspheres can carry, comprise or are otherwise coated with a nucleic acid probe, wherein the nucleic acid probe is arranged and adapted to hybridize with single-stranded nucleic acid, DNA or RNA.

Also disclosed herein are combinations of a plate frame holder and a sample plate as described above.

In some embodiments, the plate frame holder can comprise a male, female or other docking portion for firmly securing the sample plate to the plate frame holder.

Also disclosed herein are automated apparatuses comprising:

one or more reagent bead or microsphere dispensers;

a sample plate as described above; and a control system arranged and adapted to control the dispensing of reagent beads or microspheres from the one or more reagent bead or microsphere dispensers into one or more sample wells of the sample plate.

The one or more reagent bead or microsphere dispensers can comprise:

a syringe body comprising an annular chamber surrounding a longitudinal bore, wherein the annular chamber is arranged, in use, to channel or funnel reagent beads or microspheres provided within the annular chamber towards a chamber provided in the bore;

a plunger provided within the longitudinal bore; and a barrel or nozzle;

wherein the plunger is arranged, in use, to dispense a reagent bead or microsphere from the chamber into the barrel or nozzle.

Also provided herein are apparatuses for assaying a liquid for one or more analytes of interest, the apparatus comprising:

one or more reagent bead or microsphere dispensers; and a sample plate as described above.

Also disclosed herein are methods comprising:

providing a sample plate comprising one or more sample wells, wherein one or more of the sample wells comprise a base portion and one or more open through holes provided in the base portion; and retaining or securing a reagent bead or microsphere within a through hole so as to form a substantially fluid-tight circumferential seal with a wall of the base portion which defines the through hole.

Also provided herein are methods comprising:

providing a sample plate comprising one or more sample wells, wherein one or more of the sample wells comprise a base portion and one or more recesses provided in the base portion; and retaining or securing a reagent bead or microsphere within a recess so as to form a substantially fluid-tight circumferential seal with a wall of the base portion which defines the recess.

Also provided herein are methods comprising:

providing one or more reagent bead or microsphere dispensers;

providing a sample plate as described above; and controlling the dispensing of reagent beads or microspheres from the one or more reagent bead or microsphere dispensers into one or more of the sample wells.

Disclosed herein are methods of using a sample plate to analyze a sample for multiple analytes comprising:

providing a sample plate as described above;

optionally inserting one or more reagent beads or microspheres into one or more through holes or recesses of a sample well; and adding a sample to the sample well.

The reagent beads or microspheres can be inserted into one or more of the pockets, recesses or bores of the sample wells either by the sample plate manufacturer of by the end user.

Disclosed herein are methods of using an Enzyme Linked Immunosorbent Assay (ELISA) to detect an antigen or an antibody in a sample comprising:

providing a sample plate as described above;

optionally inserting one or more reagent beads or microspheres into one or more through holes or recesses of a sample well; and adding a sample to the sample well.

The reagent beads or microspheres can be inserted into one or more of the pockets, recesses or bores of the sample wells either by the sample plate manufacturer of by the end user.

Also provided herein are methods of using a nucleic acid probe to detect a DNA or RNA sequence in a sample comprising:

providing a sample plate as described above;
optionally inserting one or more reagent beads or microspheres into one or more through holes or recesses of a sample well; and
adding a sample to the sample well.

The reagent beads or microspheres can be inserted into one or more of the pockets, recesses or bores of the sample wells either by the sample plate manufacturer of by the end user.

Disclosed herein are methods for assaying for one or more analytes of interest in a sample comprising:
optionally inserting one or more reagent beads or microspheres into one or more through holes or recesses of one or more sample wells of a sample plate so as to retain or secure a reagent bead or microsphere within the through hole or recess so as to form a substantially fluid-tight circumferential seal with a wall of the base portion which defines the through hole or recess.

The reagent beads or microspheres can be inserted into one or more of the pockets, recesses or bores of the sample wells either by the sample plate manufacturer of by the end user.

Disclosed herein are methods of detecting an analyte comprising:
providing a sample plate as described above wherein one or more reagent beads or microspheres are retained or secured within one or more through holes or recesses provided in the base portion of the sample plate;
adding a sample to the sample plate; and
detecting binding of an analyte in the sample to a reagent bead or microsphere.

Some embodiments further comprise one or more of the following steps:
(i) incubating the sample plate; and/or
(ii) washing the sample plate; and/or
(iii) aspirating the sample plate; and/or
(iv) adding an enzyme conjugate to the sample plate; and/or
(v) adding a visualizing agent to the sample plate; and/or
(vi) visually analyzing the sample plate.

Provided herein are kits for performing an Enzyme Linked Immunosorbent Assay (ELISA) procedure comprising:
one or more sample plates as described above; and
a plurality of reagent beads or microspheres, the reagent beads or microspheres being coated with a reagent comprising an antibody, an antigen or another biomolecule.

Also provided herein are kits for performing a nucleic acid probe procedure comprising:
one or more sample plates as described above; and
a plurality of reagent beads or microspheres, the reagent beads or microspheres being coated with a DNA or RNA sequence.

One or more reagent beads or microspheres can be retained or secured within one or more through holes or recesses provided in the base portion of the sample plate.

According to an aspect of the disclosure there are provided kits for detecting an analyte comprising:
one or more sample plates as described above; and
a plurality of reagent beads or microspheres retained or secured within one or more through holes or recesses provided in the base portion of the sample plate so that the plurality of reagent beads or microspheres form a substantially fluid-tight circumferential seal with a wall of the base portion which defines the through hole or the recess.

Disclosed herein are methods of manufacturing a sample plate comprising:

providing a sample plate comprising one or more sample wells each having a base portion; and
forming one or more through holes or recesses in the one or more base portions, wherein the one or more through holes or recesses are arranged and adapted so as to retain or secure a reagent bead or microsphere within the through hole or recess so as to form a substantially fluid-tight circumferential seal with a wall of the base portion which defines the through hole or recess.

In some embodiments, the method of manufacturing can further comprise inserting one or more reagent beads or microspheres into the through holes or recesses so that the one or more reagent beads or microspheres form a substantially fluid-tight circumferential seal with a wall of the base portion which defines the through hole or recess.

Also provided herein are sample plates comprising a sample well, wherein the sample well comprises a base portion, wherein the base portion comprises a recess and the recess comprises a diameter less than a diameter of a bead deposited in the sample well.

The diameter of the recess is can at least about 5% smaller than the diameter of the bead.

The recess can comprise a countersunk portion.

The sample plate can comprise a plurality of sample wells.

The sample well can comprise a plurality of recesses.

The one or more recesses can comprise circular recesses.

The one or more recesses can have a circular cross-sectional shape or profile.

According to an embodiment, a bead is substantially retained or secured, in use, within the one or more recesses by an interference or friction fit with the recess or bore or with the circumference of the recess or bore.

According to an embodiment, a preset force can compress a bead and/or deform the recess so as to create or enhance an interference or friction fit with the recess or bore.

According to an embodiment, a bead forms a substantially fluid-tight seal with the recess.

In some embodiments, the one or more recesses do not comprise a tapered section.

The sample well can comprise between 2 and 20 recesses.

According to an embodiment the sample well comprises at least 10 recesses.

The plurality of recesses can be arranged circumferentially around a central portion of the sample well.

In some embodiments the central portion can comprise a central recess.

In one embodiment, the central portion does not comprise a recess.

The plurality of recesses can be arranged in a substantially symmetrical or regular manner.

According to another embodiment, the plurality of recesses are arranged in a substantially asymmetrical or irregular manner.

According to an embodiment, the plurality of recesses can be arranged in a substantially linear manner.

According to an embodiment, the plurality of recesses can be arranged in a substantially curved manner.

The plurality of sample wells can be arranged in an A×B format, wherein A and B are perpendicular axes, and the number of wells along the A axis can be greater than, less than, or equal to the number of wells along the B axis.

According to an embodiment, the number of wells along the A axis or B axis is at least 2.

The number of wells along the A axis or B axis can be between 2 and 15.

According to an embodiment, at least one of the plurality of sample wells is connected to another sample well of the plurality of samples wells by a frangible region.

The sample plate can comprise a base comprising a docking portion for securing the sample plate to a corresponding docking portion of a plate frame holder.

According to an embodiment, the sample plate can further comprise a bead.

The bead is can be attached to a probe.

The probe is can be a nucleic acid, antibody, antibody fragment, protein, peptide, aptamer, or chemical compound. According to an embodiment, the probe is an oligonucleotide.

In some embodiments, the sample plate comprises a plurality of probes, wherein a subset of the plurality of probes differs from another subset of the plurality of probes.

In some embodiments, the plurality of probes comprise at least 3 different probes.

Also provided herein are bead dispensing systems comprising:

a bead dispenser;

a sample plate comprising a sample well, wherein the sample well comprises a base portion, wherein the base portion comprises a recess and the recess comprises a diameter less than a diameter of a bead dispensed into the sample well; and a control system configured to control dispensing of the bead from the bead dispenser into the sample plate.

The bead dispenser can comprise:

a syringe body comprising an annular chamber surrounding a longitudinal bore, wherein the annular chamber is configured to channel a reagent bead within the annular chamber towards a chamber provided in the bore;

a plunger provided within the longitudinal bore; and a barrel or nozzle;

wherein the plunger is configured to dispense a bead from the chamber into the barrel or nozzle.

The bead dispenser can be configured to dispense a plurality of beads automatically.

Also disclosed herein are methods of dispensing beads comprising:

providing a bead dispenser comprising a bead;

providing a sample plate comprising a sample well, wherein the sample well comprises a base portion, wherein the base portion comprises a recess, wherein the recess comprises a diameter less than a diameter of the bead; and controlling the dispensing of the bead from the bead dispenser into the sample plate.

The dispensing can be performed automatically.

Disclosed herein are kits for detecting an analyte comprising:

a plurality of beads; and sample plate comprising a sample well, wherein the sample well comprises a base portion, wherein the base portion comprises a recess, wherein the recess comprises a diameter less than a diameter of a bead of the plurality of beads.

The plurality of beads can comprise one or more probes.

The probe can comprise a nucleic acid, antibody, antibody fragment, protein, peptide, aptamer, or chemical compound.

According to an embodiment, the probe is an oligonucleotide.

Also disclosed herein are methods of detecting an analyte comprising:

adding a sample to a sample plate comprising a sample well, wherein the sample well comprises a base portion, wherein the base portion comprises a recess, wherein the recess comprises a probe and the recess comprises a diameter less than a diameter of a bead comprising the probe; and detecting binding of an analyte in the sample with the probe.

The sample plate can comprise a plurality of probes and a plurality of analytes can be detected.

A plurality of samples can be added to the sample plate.

A sample plate is disclosed comprising one or more sample wells, wherein the one or more sample wells comprise a base portion and one or more pockets or recesses provided in the base portion, wherein the one or more pockets or recesses comprise a bore having a tapered section wherein, in use, a reagent bead or microsphere is substantially retained or secured within the bore by the tapered section.

In some embodiments, the bore having the tapered section is not a shallow or small depression in which a reagent bead or microsphere rests but in which the reagent bead or microsphere is not substantially retained or secured.

In some embodiments, in use, a reagent bead or microsphere is substantially retained or secured within the bore by an interference or friction fit with the tapered section of the bore.

In some embodiments, reagent beads are inserted into a sample plate having a plurality of tapered holes or sections which act to firmly secure or lock the reagent beads in position once inserted. A preset force can be used to insert the reagent beads. The preset force can be sufficient to compress the reagent bead and/or to deform the tapered section of the bore so as to create or enhance the interference or friction fit with the tapered section of the bore.

The sample plates disclosed herein can be particularly robust during manufacture and in subsequent processing stages including the stage of inserting reagent beads into the tapered holes and subsequent handling and processing of the sample plate. In some embodiments, the reagent beads inserted into a sample plate are not free to move in any direction and essentially become a fixed part of the sample plate. In some embodiments, the angle of the taper can be arranged so that reagent beads are locked or are otherwise firmly secured into the holes.

In some embodiments, in use, a reagent bead can be substantially retained or secured within the bore if the sample plate (i.e. the plane of the sample plate) is tipped by, for example more than about 10°, 20°, 30°, 40°, 50°, 60°, 70°, 80°, or 90° to horizontal, or is inverted.

In some embodiments, the opening to the bore and/or cross-sectional shape of the bore (i.e. at a location intermediate the opening to the bore and the base of the bore) is circular. In some embodiments, the opening and/or cross-sectional shape of the bore can be substantially circular, elliptical, oblong, triangular, square, rectangular, pentagonal, hexagonal, septagonal, octagonal, nonagonal, decagonal or polygonal.

In some embodiments, the diameter of the opening of the bore is selected from the group consisting of: (i) <0.5 mm; (ii) 0.5-1.0 mm; (iii) 1.0-1.5 mm; (iv) 1.5-2.0 mm; (v) 2.0-2.5 mm; (vi) 2.5-3.0 mm; (vii) 3.0-3.5 mm; (viii) 3.5-4.0 mm; (ix) 4.0-4.5 mm; (x) 4.5-5.0 mm; (xi) <5.0 mm; and (xii) >5.0 mm.

In some embodiments, the diameter of the opening of the bore is greater than the diameter of the reagent bead or microsphere. In some embodiments, the opening of the bore has a cross-sectional shape that is other than circular. In some embodiments, the smallest span of the cross-sectional shape of the bore at the opening is greater than the diameter of the reagent bead or microsphere.

In one embodiment, a diameter of the bore at a location intermediate the opening of the bore and the base of the bore can be at least 5% smaller than the diameter of the reagent bead or microsphere and/or is at least 5% smaller than the diameter of the opening of the bore. In some embodiments, the bore has a cross-sectional shape that is other than circular and the smallest span of the cross-sectional shape of the bore at a location intermediate the opening of the bore and the base of the bore is at least 5% smaller than the diameter of the reagent bead or microsphere and/or is at least 5% smaller than the diameter of the opening of the bore.

In some embodiments, a diameter of the bore at a location intermediate the opening of the bore and the base of the bore is selected from the group consisting of: (i) <0.5 mm; (ii) 0.5-1.0 mm; (iii) 1.0-1.5 mm; (iv) 1.5-2.0 mm; (v) 2.0-2.5 mm; (vi) 2.5-3.0 mm; (vii) 3.0-3.5 mm; (viii) 3.5-4.0 mm; (ix) 4.0-4.5 mm; (x) 4.5-5.0 mm; (xi) <5.0 mm; and (xii) >5.0 mm.

In some embodiments, the tapered section of the bore is substantially linearly tapered. For example, the diameter or circumference of the bore varies (e.g. decreases) substantially linearly with the depth of the bore. In some embodiments, the bore has a cross-sectional shape that is other than circular and a cross-sectional dimension (e.g. the smallest span of the cross-sectional shape of the bore) or the perimeter of the cross-sectional shape of the bore varies (e.g. decreases) substantially linearly with the depth of the bore.

In some embodiments, the reagent beads are opaque and signal is only detected from the top of the bead. In some embodiments, the bottom of the bead below a press fit or interference fit line does not come into contact with sample fluid. In some embodiments, in use, a reagent bead forms a substantially fluid-tight seal with either the cylindrical or tapered section of the bore so as to substantially prevent fluid from flowing from the sample well past the reagent bead. A sample plate with inserted reagent beads, according to some embodiments, therefore resembles an empty conventional sample well.

In some embodiments, the reagent beads protrude above the bottom of the sample well. In some embodiments, the reagent beads do not form a moat region around the upper portion of the bead. In some embodiments, the reagent beads do not trap fluid.

In some embodiments, the reagent beads can be arranged so as not to protrude above the bottom of the sample well. In some embodiments, reagent beads are protected and are not susceptible to damage through handling, pipetting or washing. In some embodiments, the bore depth at which the diameter of the bore becomes less than the diameter of the reagent bead is equal to or greater than the radius of the reagent bead. In some embodiments, the reagent beads do not protrude above the bottom of the sample well. In some embodiments, the bore has a cross-sectional shape that is other than circular and the bore depth at which the smallest span of the cross-sectional shape of the bore becomes less than the diameter of the reagent bead is equal to or greater than the radius of the reagent bead.

Beads can be pressed or inserted into the pockets, recesses or bores formed in the base portion of the sample wells. The tops of the reagent beads once inserted can protrude above the bottom of the sample well, or alternatively, can be flush or level with the bottom of the sample well.

In some embodiments, a 2 mm bead can be arranged to protrude 0.5 mm above the bottom of the base portion of the sample well. According to some embodiments, one or more of the reagent beads can be arranged to protrude a distance of 0-5%, 5-10%, 10-15%, 15-20%, 20-25%, 25-30%, 30-35%, 35-40% or >40% of the diameter of the bead above the bottom of the base portion of the sample well.

According to some embodiments, the depth of the bore is selected from the group consisting of: (i) <0.5 mm; (ii) 0.5-1.0 mm; (iii) 1.0-1.5 mm; (iv) 1.5-2.0 mm; (v) 2.0-2.5 mm; (vi) 2.5-3.0 mm; (vii) 3.0-3.5 mm; (viii) 3.5-4.0 mm; (ix) 4.0-4.5 mm; (x) 4.5-5.0 mm; (xi) <5.0 mm; and (xii) >5.0 mm.

In some embodiments, in use, the reagent bead does not contact the base of the bore. In some embodiments, a reagent bead may contact the base of the bore.

In some embodiments, the reagent beads can be inserted so that they are flush with the bottom of the well and the sample plate can be used with known automated microplate processing systems requiring only minimal hardware modifications. Furthermore, the sample well according to such an embodiment is essentially a cylinder having proportions which are similar to that of a well of a conventional microplate so the fluid and other handling characteristics of the sample well are well known. Processing steps according to such an embodiment such as pipetting, mixing, washing and incubation follow the same type of fluid characteristics that conventional microplates go through.

The sample plate according can have a fluid capacity of approximately 800 µl. In some embodiments, in use, only a small fraction of the total fluid capacity of a sample well is required in order to cover all the reagent beads disposed in the base of the sample plate.

In some embodiments, fluid can be dispensed directly into the centre or central region of a sample well and the sample plate may be arranged so that no pockets, recesses or bores for securing reagent beads are arranged in the central region of the sample well. In some embodiments, reagent which coats the reagent beads is not inadvertently washed off the reagent beads by the force of the fluid jet from a wash head or pipette tip.

The sample plate according some embodiments, enables multiple tests to be carried out in a single sample well. This can be achieved by inserting different reagent beads into separate bores in the same sample well thereby enabling multiplexing to be performed. In some embodiments, reagent beads can be pressed into tapered or non-tapered holes in the base of the well as desired which results in a high degree of flexibility and the ability to use the entire sample well with a high efficiency.

In some embodiments, a sample plate can comprise one or more 12 mm diameter sample wells. Each sample well can have a cross sectional surface area of 58 mm2 and in total 54 sample wells of this size can be fitted into a conventional microplate footprint. Within each sample well a varied number of beads can be inserted. The bores in a sample well can have different diameters to accommodate different size reagent beads if desired.

According to other embodiments, one or more sample wells may comprise 6×3.0 mm diameter pockets, recesses or bores, 10×2.0 mm diameter pockets, recesses or bores or 21×1.75 mm pockets, recesses or bores. The central region of the sample well can be kept free of pockets, recesses or bores. The pockets, recesses or bores may be arranged in a circle or two or more concentric circles or other patterns about the central region of the sample well.

According to an embodiment, a sample plate having an array of 9×6 sample wells may be provided. If six pockets, recesses or bores are provided per sample well, then the sample plate can accommodate 324 reagent beads per plate. If 10 pockets, recesses or bores are provided per sample well, then the sample plate can accommodate 540 reagent beads per plate. If 21 pockets, recesses or bores are provided per sample well, then the sample plate can accommodate 1134 reagent beads per plate.

In some embodiments, the sample plate according to the present invention is relatively simple to manufacture compared with other known arrangements. The sample plate can be manufactured by moulding using an open and shut tool so that the manufacturability is high and reliable. The injection mould tool design used to form the sample plates is simple and does not require the use of undercuts or thin features to mould. As a result, the production of sample plates having different formats can be readily achieved. A tool that produces a sample well with six pockets or bores can be readily adapted to produce a sample well having a different number (e.g. 21) of pockets.

In some embodiments, validation of different well designs and formats can be achieved simply since the test protocols can remain essentially the same. In some embodiments, pipetting and incubation do not change and the washing procedure would only requires, at most, a minor alteration to the aspirate routine.

The tapered section or bore can have a taper selected from the group consisting of: (i) <0.5°; (ii) 0.5°; (iii) 0.5-1°; (iv) 1-2°; (v) 2-4°; (vi) 4-6°; (vii) 6-8°; (viii) 8-10°; and (ix) >10°. Alternatively, through holes or bores provided in the base portion may be cylindrical and non-tapered.

In some embodiments, arrangement of the pockets or recesses provided in the base portion may comprise a chamber having a retention member, membrane, lip or annular portion. A reagent bead or microsphere may be inserted, in use, past or through the retention member, membrane, lip or annular portion into the chamber and may be substantially retained or secured within the chamber by the retention member, membrane, lip or annular portion.

The one or more pockets, recesses or bores can comprise a countersunk or enlarged portion for facilitating the insertion of a reagent bead or microsphere into one or more of the pockets, recesses or bores.

The one or more sample wells can comprise at least 1, 2, 3, 4, 5, 6, 7, 8, 9, 10, 11, 12, 13, 14, 15, 16, 17, 18, 19, 20 or 21 pockets or recesses each comprising a bore having a tapered or non-tapered section and which are each arranged and adapted to receive, in use, a reagent bead or microsphere.

The one or more pockets, recesses or bores provided in the base portion can be arranged:
(i) circumferentially around a central portion of the sample well; and/or (ii) with a plurality of pockets or recesses arranged circumferentially around one more central pockets or recesses; and/or (iii) in a substantially close-packed manner; and/or (iv) in a substantially symmetrical or asymmetrical manner; and/or (v) in a substantially linear or curved manner; and/or (vi) in a substantially regular or irregular manner; and/or (vii) in an array; and/or (viii) in a circle or two or more concentric circles with no pocket, recess or bore located at the centre of the base portion.

The sample plate can be fabricated or otherwise made from polystyrene.

The sample plate may comprise either a strip or an array format. For example, according to an embodiment the sample plate may comprise a 6×1 strip of sample wells. According to another embodiment the sample plate may comprise nine 6×1 sample strips of sample wells.

According to an embodiment one or more of the sample wells may be interconnected to one or more other sample wells by one or more frangible regions or connections so that the sample plate can be separated by a user into a plurality of smaller sample plates, sample strips or individual sample wells. This enables a sample plate to be snapped or broken into a plurality of smaller sample plates. For example, a 6×1 strip of sample wells may be snapped into six individual sample wells or into two 3×1 sample strips.

According to an embodiment individual sample wells, sample strips and sample plates are made from polypropylene. Sample wells, sample strips and sample plates can be made from a non-binding material such as polypropylene to ensure non-specific binding in the well is kept to a minimum.

A plate frame arranged to hold a plurality of sample wells, sample strips or one or more sample plates can be made from a plastic such as Acrylonitrile Butadiene Styrene ("ABS"). The plate frame can be made from a material which provides high rigidity and which ensures that sample wells, sample strips or one or more sample plates are held securely in place and remain flat after sample wells, sample strips or sample plates are secured into the plate frame. The plate frame can be sufficiently robust to withstand handling by a user.

One or more of the sample wells may be interconnected to one or more other sample wells by one or more frangible regions or connections so that the sample plate can be separated by a user into a plurality of smaller sample plates, sample strips or individual sample wells.

According to an aspect of the disclosure, there is provided a computer program executable by the control system of an automated apparatus, the automated apparatus comprising one or more reagent bead or microsphere dispensers, the computer program being arranged to cause the control system:
(i) to control the dispensing of reagent beads or microspheres from the one or more reagent bead or microsphere dispensers into one or more sample wells of a sample plate as disclosed above.

According to an aspect of the disclosure there is provided a computer readable medium comprising computer executable instructions stored on the computer readable medium, the instructions being arranged to be executable by a control system of an automated apparatus, the automated apparatus comprising one or more reagent bead or microsphere dispensers, the computer program being arranged to cause the control system:
(i) to control the dispensing of reagent beads or microspheres from the one or more reagent bead or microsphere dispensers into one or more sample wells of a sample plate as disclosed above.

The computer readable medium can be selected from the group consisting of: (i) a ROM; (ii) an EAROM; (iii) an EPROM; (iv) an EEPROM; (v) a flash memory; (vi) an optical disk; (vii) a RAM; and (viii) a hard disk drive.

In some embodiments, at least some or substantially all of the reagent beads or microspheres which are dispensed, in use, into one or more of the pockets, recesses or bores carry or comprise a reagent, wherein the reagent is arranged and adapted: (i) to analyze samples; and/or (ii) to analyze samples by nucleic acid amplification reactions; and/or (iii) to analyze samples by polymerase chain reactions (PCR); and/or (iv) to analyze samples by an immunoassay process; and/or (v) to analyze samples by using a hybridization probe technique.

In some embodiments, at least some or substantially all of the reagent beads or microspheres which are dispensed, in use, into one or more of the pockets, recesses or bores comprise polystyrene, plastic or a polymer.

The sample plate disclosed herein can comprise one or more beads. The bead can be a microparticle, particle, microsphere, or grammatical equivalents. The bead composition is dependent on the type of assay being performed. The bead may be composed of plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles, Teflon or any combination thereof. In one embodiment, a bead comprises polystyrene, plastic, a polymer, or a combination thereof. In another embodiment, a bead comprises a ferrous or magnetic coating or has a ferrous or magnetic property. In yet another embodiment, a bead comprises an anti-static coating or has an anti-static property. The bead used in the sample plate reagent beads can be translucent, slightly translucent, or opaque. Commercially available beads can also be used.

The beads need not be spherical and may be of irregular shape. In addition, the beads may be porous. The bead size may range from nanometers to millimeters. The bead may have a diameter of at least 0.1 mm. The bead may have a diameter of between 0.1 mm and 10 mm. In one embodiment, the bead may have a diameter of greater than about 0.5 mm; 0.5-1.0 mm; 1.0-1.5 mm; 1.5-2.0 mm; 2.0-2.5 mm; 2.5-3.0 mm; 3.0-3.5 mm; 3.5-4.0 mm; 4.0-4.5 mm; 4.5-5.0 mm; or greater than about 5.0 mm. The bead may have a diameter greater than, equal to, or less than the diameter of a recess, pocket, or bore of a sample well. For example, the bead may have a diameter less than the diameter of a recess, pocket, or bore of a sample well, wherein the recess, pocket or bore comprises a tapered section. In yet another embodiment, the bead may have a diameter greater than the diameter of a recess, pocket, or bore of a sample well. For example, the recess, pocket, or bore may not comprise a tapered section. The diameter of a bead to be deposited, or present, in the sample plate, can be at least about 5, 10, 15, 20, 35, 30, 35, 40, 45, 50, 55, 60, 65, 70, 75, 80, 85, 90, 95, or 100% greater than the diameter of a recess of the sample plate. In one embodiment, the bead present in a sample plate does not touch the bottom of a sample plate, such as a base portion of a sample well.

A bead within the sample plate may comprise a reagent or probe, or be coated with a reagent or probe. The reagent or probe can be used to analyze a sample, such as by detecting an analyte. The probe or reagent can be attached to the bead. The attachment can be a covalent or non-covalent interaction. The probe can be a nucleic acid, antibody, antibody fragment, protein, peptide, aptamer, or chemical compound. For example, the probe can be an oligonucleotide. In one embodiment, the probe can be used to detect an analyte in a biological sample. In yet another embodiment, the probe can be used to for drug screening. For example, a library of compounds or antibodies can be screened for its binding ability to a protein or nucleic acid probe.

The probe can be used to provide detect a biomarker for a diagnosis or prognosis of a disease or condition, drug response or potential drug response, or for monitoring the progression of a disease or condition. For example, the probe can be an antibody or fragment thereof that is used to detect an antigen that is a biomarker for cancer. In another embodiment, the probe can be an antigen, peptide or protein, which is used to detect an antibody in a sample, which can be an indicative of a disease or condition.

The sample plate disclosed herein can comprise a plurality of probes, wherein a subset of the plurality differs from another subset of the plurality. The plurality of probes can be attached to beads. The different probes can be used to detect different analytes, thus allowing multiplexing with the sample plates disclosed herein. The sample plate can comprise at least 2, 3, 4, 5, 6, 7, 8, 9, 10, 11, 12, 13, 14, 15, 16, 17, 18, 19, or 20 different probes. The probes can be of the same type (for example, different antibodies) or of a different type (for example, a combination of nucleic acid probe(s) and antigen(s)).

According to an embodiment the one or more of the reagent bead or microsphere dispensers can comprise a tube containing, in use, a plurality of reagent beads or microspheres.

The apparatus can further comprise one or more sensors for sensing whether or not one or more reagents beads have been dispensed from one or more of the reagent bead or microsphere dispensers.

The apparatus can further comprise a translation stage for moving the sample plate relative to one or more reagent bead or microsphere dispensers.

The control system can be arranged and adapted to control the translation stage so that one or more reagent beads or microspheres from a reagent bead or microsphere dispenser are dispensed sequentially into different reagent bead or microsphere receiving chambers by moving the sample plate relative to the reagent bead or microsphere dispenser.

According to an embodiment the apparatus further comprises a fluid dispensing device for dispensing fluid into the sample wells of a sample plate.

The fluid dispensing device can be arranged and adapted to dispense x ml of fluid at a time into the one or more fluid receiving areas of one or more sample wells, wherein x is preferably selected from the group consisting of: (i) <10; (ii) 10-20; (iii) 20-30; (iv) 30-40; (v) 40-50; (vi) 50-60; (vii) 60-70; (viii) 70-80; (ix) 80-90; (x) 90-100; (xi) 100-110; (xii) 110-120; (xiii) 120-130; (xiv) 130-140; (xv) 140-150; (xvi) 150-160; (xvii) 160-170; (xviii) 170-180; (xix) 180-190; (xx) 190-200; and (xxi) >200.

In some embodiments, the fluid dispensing device is arranged and adapted to dispense about 1 µL, µL, 2 µL, 3 µL, 4 µL, 5 µL, 6 µL, 7 µL, 8 µL, 9 µL, 10 µL, 11 µL, 12 µL, 13 µL, 14 µL, 15 µL, 16 µL, 17 µL, 18 µL, 19 µL, 20 µL, 21 µL, 22 µL, 23 µL, 24 µL, 25 µL, 26 µL, 27 µL, 28 µL, 29 µL, 30 µL, 31 µL, 32 µL, 33 µL, 34 µL, 35 µL, 36 µL, 37 µL, 38 µL, 39 µL, 40 µL, 41 µL, 42 µL, 43 µL, 44 µL, 45 µL, 46 µL, 47 µL, 48 µL, 49 µL, 50 µL, 51 µL, 52 µL, 53 µL, 54 µL, 55 µL, 56 µL, 57 µL, 58 µL, 59 µL, 60 µL, 61 µL, 62 µL, 63 µL, 64 µL, 65 µL, 66 µL, 67 µL, 68 µL, 69 µL, 70 µL, 71 µL, 72 µL, 73 µL, 74 µL, 75 µL, 76 µL, 77 µL, 78 µL, 79 µL, 80 µL, 81 µL, 82 µL, 83 µL, 84 µL, 85 µL, 86 µL, 87 µL, 88 µL, 89 µL, 90 µL, 91 µL, 92 µL, 93 µL, 94 µL, 95 µL, 96 µL, 97 µL, 98 µL, 99 µL, 100 µL, 101 µL, 102 µL, 103 µL, 104 µL, 105 µL, 106 µL, 107 µL, 108 µL, 109 µL, 110 µL, 111 µL, 112 µL, 113 µL, 114 µL, 115 µL, 116 µL, 117 µL, 118 µL, 119 µL, 120 µL, 121 µL, 122 µL, 123 µL, 124 µL, 125 µL, 126 µL, 127 µL, 128 µL, 129 µL, 130 µL, 131 µL, 132 µL, 133 µL, 134 µL, 135 µL, 136 µL, 137 µL, 138 µL, 139 µL, 140 µL, 141 µL, 142 µL, 143 µL, 144 µL, 145 µL, 146 µL, 147 µL, 148 µL, 149 µL, 150 µL, 151 µL, 152 µL, 153 µL, 154 µL, 155 µL, 156 µL, 157 µL, 158 µL, 159 µL, 160 µL, 161 µL, 162 µL, 163 µL, 164 µL, 165 µL, 166 µL, 167 µL, 168 µL, 169 µL, 170 µL, 171 µL, 172 µL, 173 µL, 174 µL, 175 µL, 176 µL, 177 µL, 178 µL, 179 µL, 180 µL, 181 µL, 182 µL, 183 µL, 184 µL, 185 µL, 186 µL, 187 µL, 188 µL, 189 µL, 190 µL, 191 µL, 192 µL, 193 µL, 194 µL, 195 µL, 196 µL, 197 µL, 198 µL, 199 µL, 200 µL, or more fluid at a time into the one or more fluid receiving areas of one or more sample wells.

According to an embodiment the apparatus further comprises an image analysis device or camera for determining whether or not a reagent bead or microsphere has been dispensed or is otherwise present in a pocket, recess or bore of the sample plate.

The sample plate can have a first color (or is transparent) and the reagent beads or microspheres can have a second different color which contrasts with the first color (or transparency) in order to facilitate visual detection of the presence or absence of a reagent bead or microsphere in a pocket, recess or bore of the sample plate.

According to an embodiment the sample plate may further comprise a luminescence or fluorescence marker.

The apparatus may further comprise a luminescence or fluorescence detecting device for determining whether or not a reagent bead or microsphere has been dispensed or is otherwise present in a pocket, recess or bore of the sample plate by determining whether or not a reagent bead or microsphere obstructs or partially obstructs the luminescence or fluorescence marker.

The apparatus may further comprise a magnetic and/or electrical and/or capacitive and/or mechanical sensor for sensing whether or not a reagent bead or microsphere has been dispensed or is otherwise present in a pocket, recess or bore of a sample plate.

The control system may determine the number of reagent beads or microspheres present and/or the number of reagent beads or microspheres absent and/or the number of reagent beads or microspheres dispensed and/or the number of reagent beads or microspheres desired to be dispensed in a sample well.

According to an embodiment the control system may measure and/or adjust the volume of fluid dispensed or desired to be dispensed into a sample well dependent upon the number of reagent beads or microspheres determined to be present and/or absent and/or dispensed and/or desired to be dispensed in the sample well.

The control system may be arranged and adapted to ensure that the upper surface of at least some or substantially all reagent beads or microspheres located in the bores of a sample well are at least partially or fully immersed by a fluid when the fluid is dispensed into the sample well.

The control system is preferably arranged and adapted to ensure that the height of fluid dispensed into a sample well remains substantially constant irrespective of the number of reagent beads or microspheres present, absent, dispensed or desired to be dispensed into the sample well.

BRIEF DESCRIPTION OF THE DRAWINGS

Various embodiments of the present invention will now be described, by way of example only, and with reference to the accompanying drawings in which:

FIG. 1 shows a sample well of a sample plate according to an embodiment of the present invention;

FIG. 7A shows a reagent bead or microsphere dispenser being transported by a reagent bead or microsphere syringe pick-up device and FIG. 7B shows a reagent bead or microsphere in the process of being dispensed from a reagent bead or microsphere dispenser by a plunger mechanism which is actuated by the reagent bead or microsphere syringe pick-up device;

FIG. 8A shows a reagent bead or microsphere syringe in the process of being ejected from the reagent bead or microsphere syringe pick-up device and FIG. 8B shows the reagent bead or microsphere syringe having been ejected from the reagent bead or microsphere pick-up device;

INCORPORATION BY REFERENCE

Figure 2A:
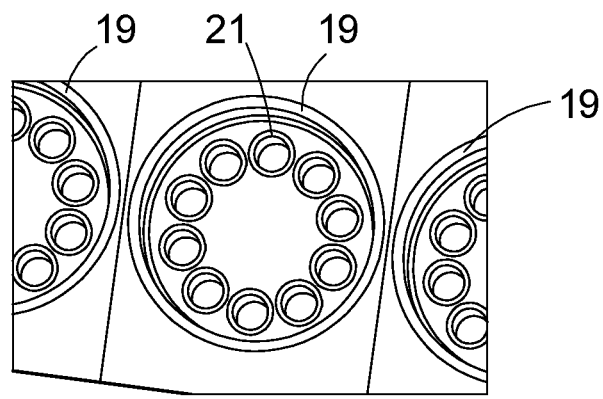
FIG. 2A shows a plan view of a sample well of a sample plate according to an embodiment.

All publications, patents, and patent applications mentioned in this specification are herein incorporated by reference to the same extent as if each individual publication, patent, or patent application was specifically and individually indicated to be incorporated by reference.

DETAILED DESCRIPTION

An embodiment of the present invention will now be described with reference to FIG. 1. A sample plate is provided that can comprise a plurality of sample wells 19 (in one embodiment, a sample plate can be provided which comprises only a single sample well 19). According to one embodiment, the sample plate may comprise a 9×6 array of sample wells 19. A single sample well 19 is shown in FIG. 1 for ease of illustration. Embodiments are also contemplated wherein the sample plate may comprise a strip of sample wells 19 e.g. the sample plate may comprise, for example, a sample strip comprising an 1×9 or an 1×6 array of sample wells 19.

Each sample well 19 can comprise a plurality of pockets, recesses or bores 21 which are provided in the base of the sample well 19. In the particular embodiment shown in FIG. 1 the sample well 19 comprises ten pockets, recesses or bores 21 which are formed or otherwise provided in the base of a sample well 19. Other embodiments are contemplated wherein a different number of pockets, recesses or bores 21 may be provided in the base of the sample well 19. For example, according to alternative embodiments at least some or all of the sample wells 19 provided in a sample plate may comprise 1, 2, 3, 4, 5, 6, 7, 8, 9, 11, 12, 13, 14, 15, 16, 17, 18, 19, 20, 21 or >21 pockets, recesses or bores 21.

The pockets, recesses or bores 21 can be provided around the edge or perimeter of the sample well 19 and the centre or central region of the base of the sample well 19 can be substantially flat and free from pockets, recesses or bores 21.

According to an embodiment a plurality of reagent beads or microspheres each having a diameter of 1.75 or 2 mm may be loaded into a reagent bead or microsphere dispenser. According to another embodiment a reagent bead or microsphere dispensers may be provided which is arranged to handle reagent beads or microspheres having a diameter other than 1.75 mm or 2 mm. Other embodiments are also contemplated wherein reagent beads or microspheres in a first reagent bead or microsphere dispenser may have a first diameter and wherein reagent beads or microspheres in a second different reagent bead or microsphere dispenser may have a second different diameter. Other embodiments are also contemplated wherein the reagent beads or microspheres loaded into a particular reagent bead or microsphere dispenser may have a plurality or mixture of different diameters.

The reagent beads or microspheres may be pre-loaded or pre-inserted into the pockets, recesses or bores 21 by a sample plate manufacturer. Alternatively, an end-user may load or insert the reagent beads or microspheres into the pockets, recesses or bores 21.

The reagent beads or microspheres can comprise a polystyrene, plastic or polymer core. The reagent beads or microspheres may be coated with a reagent (e.g. an antibody or antigen) which can be used to analyze samples. According to an embodiment the reagent may be used to analyze samples by polymerase chain reactions (PCR) or as part of an immunoassay procedure. Alternatively, according to another embodiment the reagent may comprise a DNA or RNA sequence which is used as a hybridization probe to detect the presence of complementary DNA or RNA sequences in a sample. The reagent beads or microspheres may also be coated with an anti-static coating or may have an anti-static property.

A fluid to be tested can be dispensed into a sample well 19 of a sample plate. The fluid may, for example, comprise a sample of blood, serum, saliva or urine taken from a patient.

According to an embodiment, about 10-200 ml of fluid sample may be dispensed into each sample well 19 of a sample plate, e.g., about 10 mL, 11 mL, 12 mL, 13 mL, 14 mL, 15 mL, 16 mL, 17 mL, 18 mL, 19 mL, 20 mL, 21 mL, 22 mL, 23 mL, 24 mL, 25 mL, 26 mL, 27 mL, 28 mL, 29 mL, 30 mL, 31 mL, 32 mL, 33 mL, 34 mL, 35 mL, 36 mL, 37 mL, 38 mL, 39 mL, 40 mL, 41 mL, 42 mL, 43 mL, 44 mL, 45 mL, 46 mL, 47 mL, 48 mL, 49 mL, 50 mL, 51 mL, 52 mL, 53 mL, 54 mL, 55 mL, 56 mL, 57 mL, 58 mL, 59 mL, 60 mL, 61 mL, 62 mL, 63 mL, 64 mL, 65 mL, 66 mL, 67 mL, 68 mL, 69 mL, 70 mL, 71 mL, 72 mL, 73 mL, 74 mL, 75 mL, 76 mL, 77 mL, 78 mL, 79 mL, 80 mL, 81 mL, 82 mL, 83 mL, 84 mL, 85 mL, 86 mL, 87 mL, 88 mL, 89 mL, 90 mL, 91 mL, 92 mL, 93 mL, 94 mL, 95 mL, 96 mL, 97 mL, 98 mL, 99 mL, 100 mL, 101 mL, 102 mL, 103 mL, 104 mL, 105 mL, 106 mL, 107 mL, 108 mL, 109 mL, 110 mL, 111 mL, 112 mL, 113 mL, 114 mL, 115 mL, 116 mL, 117 mL, 118 mL, 119 mL, 120 mL, 121 mL, 122 mL, 123 mL, 124 mL, 125 mL, 126 mL, 127 mL, 128 mL, 129 mL, 130 mL, 131 mL, 132 mL, 133 mL, 134 mL, 135 mL, 136 mL, 137 mL, 138 mL, 139 mL, 140 mL, 141 mL, 142 mL, 143 mL, 144 mL, 145 mL, 146 mL, 147 mL, 148 mL, 149 mL, 150 mL, 151 mL, 152 mL, 153 mL, 154 mL, 155 mL, 156 mL, 157 mL, 158 mL, 159 mL, 160 mL, 161 mL, 162 mL, 163 mL, 164 mL, 165 mL, 166 mL, 167 mL, 168 mL, 169 mL, 170 mL, 171 mL, 172 mL, 173 mL, 174 mL, 175 mL, 176 mL, 177 mL, 178 mL, 179 mL, 180 mL, 181 mL, 182 mL, 183 mL, 184 mL, 185 mL, 186 mL, 187 mL, 188 mL, 189 mL, 190 mL, 191 mL, 192 mL, 193 mL, 194 mL, 195 mL, 196 mL, 197 mL, 198 mL, 199 mL, 200 mL. According to the preferred embodiment less fluid may be dispensed into each sample well 19 compared with a conventional sample plate.

According to another embodiment, about 10-200 µL of fluid sample may be dispensed into each sample well 19 of a sample plate, e.g., about 10 µL, 11 µL, 12 µL, 13 µL, 14 µL, 15 µL, 16 µL, 17 µL, 18 µL, 19 µL, 20 µL, 21 µL, 22 µL, 23 µL, 24 µL, 25 µL, 26 µL, 27 µL, 28 µL, 29 µL, 30 µL, 31 µL, 32 µL, 33 µL, 34 µL, 35 µL, 36 µL, 37 µL, 38 µL, 39 µL, 40 µL, 41 µL, 42 µL, 43 µL, 44 µL, 45 µL, 46 µL, 47 µL, 48

μL, 49 μL, 50 μL, 51 μL, 52 μL, 53 μL, 54 μL, 55 μL, 56 μL, 57 μL, 58 μL, 59 μL, 60 μL, 61 μL, 62 μL, 63 μL, 64 μL, 65 μL, 66 μL, 67 μL, 68 μL, 69 μL, 70 μL, 71 μL, 72 μL, 73 μL, 74 μL, 75 μL, 76 μL, 77 μL, 78 μL, 79 μL, 80 μL, 81 μL, 82 μL, 83 μL, 84 μL, 85 μL, 86 μL, 87 μL, 88 μL, 89 μL, 90 μL, 91 μL, 92 μL, 93 μL, 94 μL, 95 μL, 96 μL, 97 μL, 98 μL, 99 μL, 100 μL, 101 μL, 102 μL, 103 μL, 104 μL, 105 μL, 106 μL, 107 μL, 108 μL, 109 μL, 110 μL, 111 μL, 112 μL, 113 μL, 114 μL, 115 μL, 116 μL, 117 μL, 118 μL, 119 μL, 120 μL, 121 μL, 122 μL, 123 μL, 124 μL, 125 μL, 126 μL, 127 μL, 128 μL, 129 μL, 130 μL, 131 μL, 132 μL, 133 μL, 134 μL, 135 μL, 136 μL, 137 μL, 138 μL, 139 μL, 140 μL, 141 μL, 142 μL, 143 μL, 144 μL, 145 μL, 146 μL, 147 μL, 148 μL, 149 μL, 150 μL, 151 μL, 152 μL, 153 μL, 154 μL, 155 μL, 156 μL, 157 μL, 158 μL, 159 μL, 160 μL, 161 μL, 162 μL, 163 μL, 164 μL, 165 μL, 166 μL, 167 μL, 168 μL, 169 μL, 170 μL, 171 μL, 172 μL, 173 μL, 174 μL, 175 μL, 176 μL, 177 μL, 178 μL, 179 μL, 180 μL, 181 μL, 182 μL, 183 μL, 184 μL, 185 μL, 186 μL, 187 μL, 188 μL, 189 μL, 190 μL, 191 μL, 192 μL, 193 μL, 194 μL, 195 μL, 196 μL, 197 μL, 198 μL, 199 μL, or 200 μL.

According to an embodiment a control system may be used to determine the location and/or type of reagent beads or microspheres which have been dispensed into the bores 21 of a sample well 19. Alternatively, the reagent beads or microspheres may be pre-loaded into the bores 21 of the sample wells 19. The control system may also determine into which bores 21 (if any) additional reagent beads or microspheres need to be dispensed. Once sample fluid has been dispensed into a sample well 19, the control system may check that an appropriate amount of sample fluid has been dispensed and that all the reagent beads or microspheres are at least partially or are fully immersed by the sample fluid.

The volume of sample fluid to be dispensed into a sample well 19 may depend upon the number of bores 21 formed within a sample well 19, the diameter of the reagent beads or microspheres which are dispensed or pre-loaded into the bores 21 and the extent to which reagent beads or microspheres protrude into the bottom of the sample well 19. The control system may be used to vary the amount of sample fluid dispensed into a sample well 19 so that reagent beads or microspheres are immersed in sample fluid to a substantially constant depth irrespective of the number of bores present in a sample well 19, the diameter of the reagent beads or microspheres or the extent to which the reagent beads or microspheres protrude into the base of the sample well 19.

Different formats of sample plates may be provided. For example, a sample plate may comprise a two dimensional array of sample wells 19 e.g. the sample plate may comprise a 4×4, 4×6, 4×8, 4×10, 4×12, 6×6, 6×8, 6×10, 6×12, 8×8, 8×10, 8×12, 10×10, 10×12 or 12×12 array of sample wells 19. According to other embodiments the sample plate may comprise a single dimensional strip of sample wells 19 e.g. the sample plate may comprise a 4×1, 6×1, 8×1, 10×1 or 12×1 strip of sample wells 19. Yet further embodiments are contemplated wherein the sample wells 19 may be provided in a format other than in an array or strip.

At least some or all of the pockets, recesses or bores 21 which are provided in the base of a sample well 19 may comprise a bore which is optionally tapered along at least a portion or substantially the whole of its length. The pockets, recesses or bores 21 may, for example, be arranged to have a 6° taper. According to an embodiment the top (or reagent bead or microsphere receiving portion) of a tapered bore may have a diameter of 1.82 mm. The base of the sample well 19 surrounding the bore may be arranged to have a countersunk portion in order to facilitate the insertion of a reagent bead or microsphere 20A;20B into the pocket, recess or bore 21. According to an embodiment the outer diameter of the countersunk portion may be 2.25 mm.

FIG. 2A shows a plan view of a sample well 19 and portions of two adjacent sample wells 19 which are provided in a sample plate. The sample wells shown in FIG. 2A form part of an array of sample wells 19 which are provided in the sample plate. Each of the sample wells 19 comprise ten pockets, recesses or bores 21 which are disposed in the bottom or base portion of the sample well 19. In use reagent beads or microspheres can be inserted into each of the pockets, recesses or bores 21 of a sample well 19 and with the embodiment shown in FIGS. 2A-2C the reagent beads or microspheres are preferably secured in the pockets, recesses or bores 21 by virtue of the diameter of the bore tapering and becoming restricted.

Figure 2B:
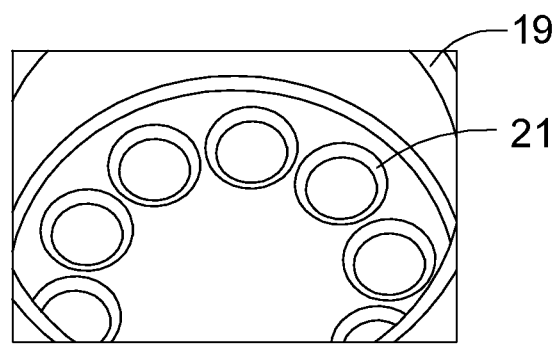
FIG. 2B shows in greater detail the bottom of a sample well according to an embodiment and FIG. 2C shows a reagent bead or microsphere dispensed in a pocket of a sample well according to an embodiment.

FIG. 2B shows in greater detail the bottom of a sample well 19 and shows a plurality of pockets, recesses or bores 21 provided in the bottom portion of the sample well 19 each of which are arranged and adapted to receive a reagent bead or microsphere. Each of the pockets, recesses or bores 21 provided in the base of the sample well 19 can also comprise a countersunk portion or region at the entrance to each tapered bore. According to an embodiment a single reagent bead or microsphere is dispensed and inserted into each pocket, recess or bore 21.

Figure 2C:
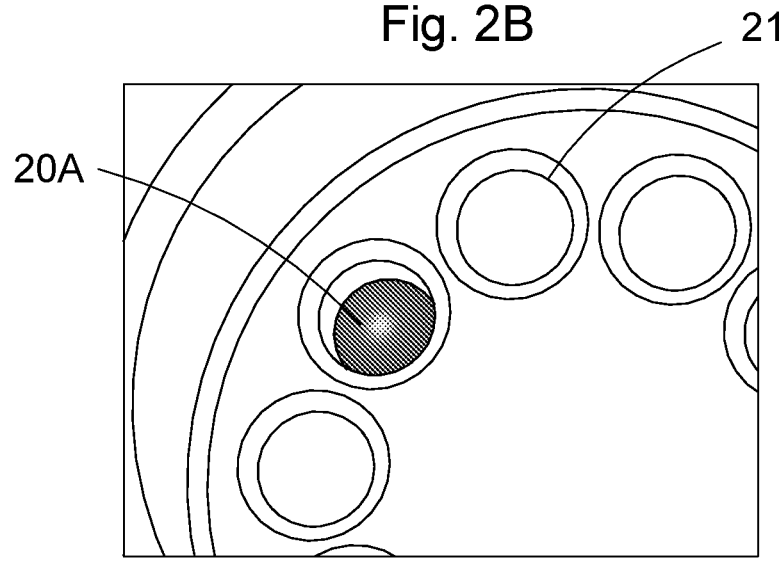

FIG. 2C shows in further detail a reagent bead or microsphere 20A disposed and securely located in a pocket, recess or bore 21 provided in the base of a sample well 19. The reagent bead or microsphere 20A is secured within the pocket, recess or bore 21. According to the embodiment shown in FIG. 2C the upper surface of the reagent bead or microsphere 20A when secured or located within the pocket, recess or bore 21 is positioned or located approximately 0.3 mm below the surface of the well bottom. Therefore, according to this embodiment reagent beads or microspheres 20A located and secured in the pockets, recesses or bores 21 provided in the bottom of a sample well 19 do not project above the entrance to or surface of the pocket, recess or bore 21 and hence do not project above the bottom surface of the sample well 19. However, according to other embodiments one or more reagent beads or microspheres may be located in one or more pockets, recesses or bores 21 provided in the base of the sample well 19 and may be located in relatively shallow pockets, recesses or bores 21 or may be located in one or more pockets, recesses or bores 21 which have a taper such that when the reagent bead or microsphere 20A is securely positioned within the pocket, recess or bore 21 then the reagent bead or microsphere projects above the entrance into or surface of the pocket, recess or bore 21 and hence projects above the bottom surface of the sample well 19. According to an embodiment reagent beads or microspheres 20A may be arranged such that they protrude 20-40% of their diameter above the bottom surface of the sample well.

Reagent beads or microspheres may be dispensed into pockets, recesses or bores 21 provided in the bottom of a sample well 19 of a sample plate by means of a reagent bead or microsphere dispenser 22 as will now be described with reference to FIGS. 3A, 3B and 4. The loading or dispensing of reagent beads or microspheres may be performed either by a sample plate manufacturer or by an end-user. A reagent bead or microsphere dispenser 22 is shown in FIG. 3A and can comprise an upper cap 23, a syringe body 24 and a barrel 25 which projects from a lower region of the syringe body 24.

Figures 3A, 3B:
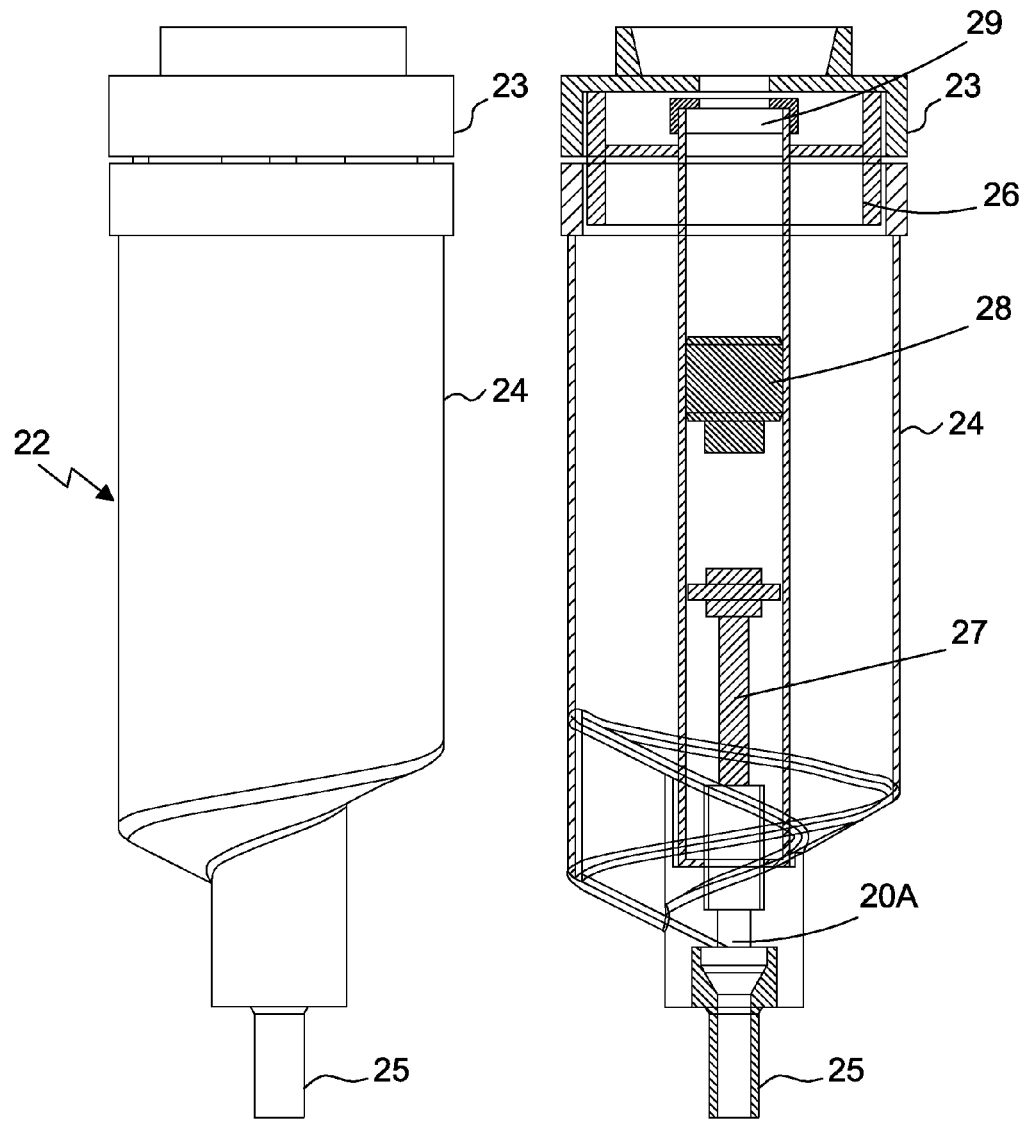
FIG. 3A shows a reagent bead or microsphere dispenser and FIG. 3B shows a cutaway view of the reagent bead or microsphere dispenser.

FIG. 3B shows a cutaway view of the reagent bead or microsphere dispenser 22 and shows that according to an embodiment the reagent bead or microsphere dispenser further comprises a plunger guide 26 which is positioned within the body of the syringe body 24. The plunger guide 26 can comprise a screw thread on the outer surface of an upper portion of the plunger guide 26. The inner surface of an upper portion of the syringe body 24 preferably comprises a complementary screw thread which engages with the screw thread provided on the outer surface of the upper portion of the plunger guide 26 so that in use the plunger guide 26 is secured or screwed firmly to the syringe body 24. The inner surface of the cap 23 can also preferably comprise a screw thread and the cap 23 also preferably screws onto the upper portion of the plunger guide 26.

A plunger 27 can be located within the plunger guide 26 and the plunger 27 may be depressed by actuating an actuator or plunger boss 28 which is located above the plunger 27 in the bore defined by the plunger guide 26. An actuator spring (not shown) is provided between the actuator or plunger boss 28 so that when the actuator or plunger boss 28 is depressed, force is transmitted to the plunger 27 via the actuator spring causing the plunger 27 to become depressed. A return spring (not shown) can be provided between the bottom portion of the plunger guide 26 and the plunger 27 so that when the actuator or plunger boss 28 is no longer depressed, both the plunger 27 and the actuator or plunger boss 28 are returned to an upper position.

Figure 4:
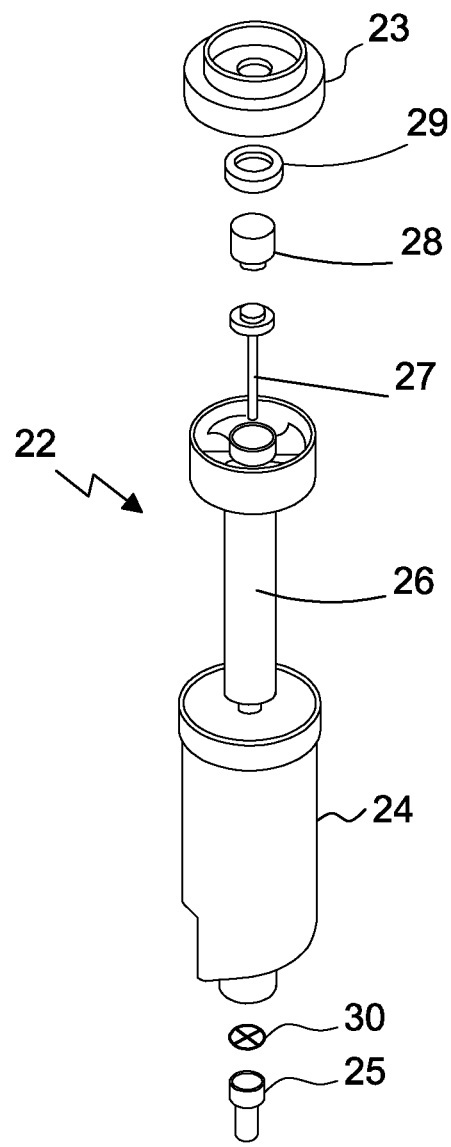
FIG. 4 shows an exploded view of the reagent bead or microsphere dispenser.

FIG. 4 shows an exploded view of the reagent bead or microsphere dispenser 22 as shown and described above with reference to FIGS. 3A and 3B. FIG. 4 also shows that a silicone member 30 can be provided within the upper portion of the barrel 25. In use, reagent beads or microspheres within the syringe body 24 can be funneled or channeled by a helical path formed in the bottom section of the syringe body 24 so that at the bottom of the syringe body 24 reagent beads or microspheres become arranged in single file or in series. The single file or series of reagent beads or microspheres leads into a chamber which can be arranged immediately above the barrel 25 and below the plunger guide 26. The chamber is shaped and arranged so as to accommodate a single reagent bead or microsphere which is positioned in a bore below the plunger 27 and above the barrel 25. When the plunger 27 is depressed, the plunger 27 can push a single reagent bead or microsphere 20A located in the chamber in a downwards direction. The single reagent bead or microsphere 20A can forced by the plunger 27 through the silicone member 30. According to an embodiment the plunger 27 continues to push or urge the reagent bead or microsphere 20A through the barrel 25 and into a pocket, recess or bore 21 of a sample well 19 which can be positioned immediately below the barrel 25 of the reagent bead or microsphere dispenser 22. The silicone member 30 can prevent the accidental release of reagent beads or microspheres from the chamber of the reagent bead or microsphere dispenser 22 into the barrel 25 of the syringe body 24.

The bottom portion of the syringe body 24 can have a helical shape and act to guide or channel reagent beads or microspheres towards the chamber disposed in a lower portion of the syringe body 24. The chamber can be arranged so that only a single reagent bead or microsphere sits above the silicone member 30 at any instance in time. The chamber is formed in the bore through which the plunger 27 travels and depression of the plunger 27 can cause a reagent bead or microsphere located in the chamber to be urged through the silicone member 30 and into the barrel 25.

A vibration mechanism may optionally be provided and may be arranged to act on the outside of the syringe body 24 so as to ensure that reagent beads or microspheres move down through syringe body 24 to the bottom portion of the syringe body 24 and line up in single file or in series ready to enter the chamber.

Reagent beads or microspheres may be pre-packed or pre-loaded into the syringe body 24 by, for example, a kit manufacturer or other supplier. Alternatively, an end-user may load the syringe body 24 with reagent beads or microspheres. According to another embodiment the sample plate manufacturer may load the syringe body 24 with reagent beads or microspheres and may supply sample plates, sample strips or individual sample wells which are pre-loaded with one or more reagent beads or microspheres.

Figure 5:
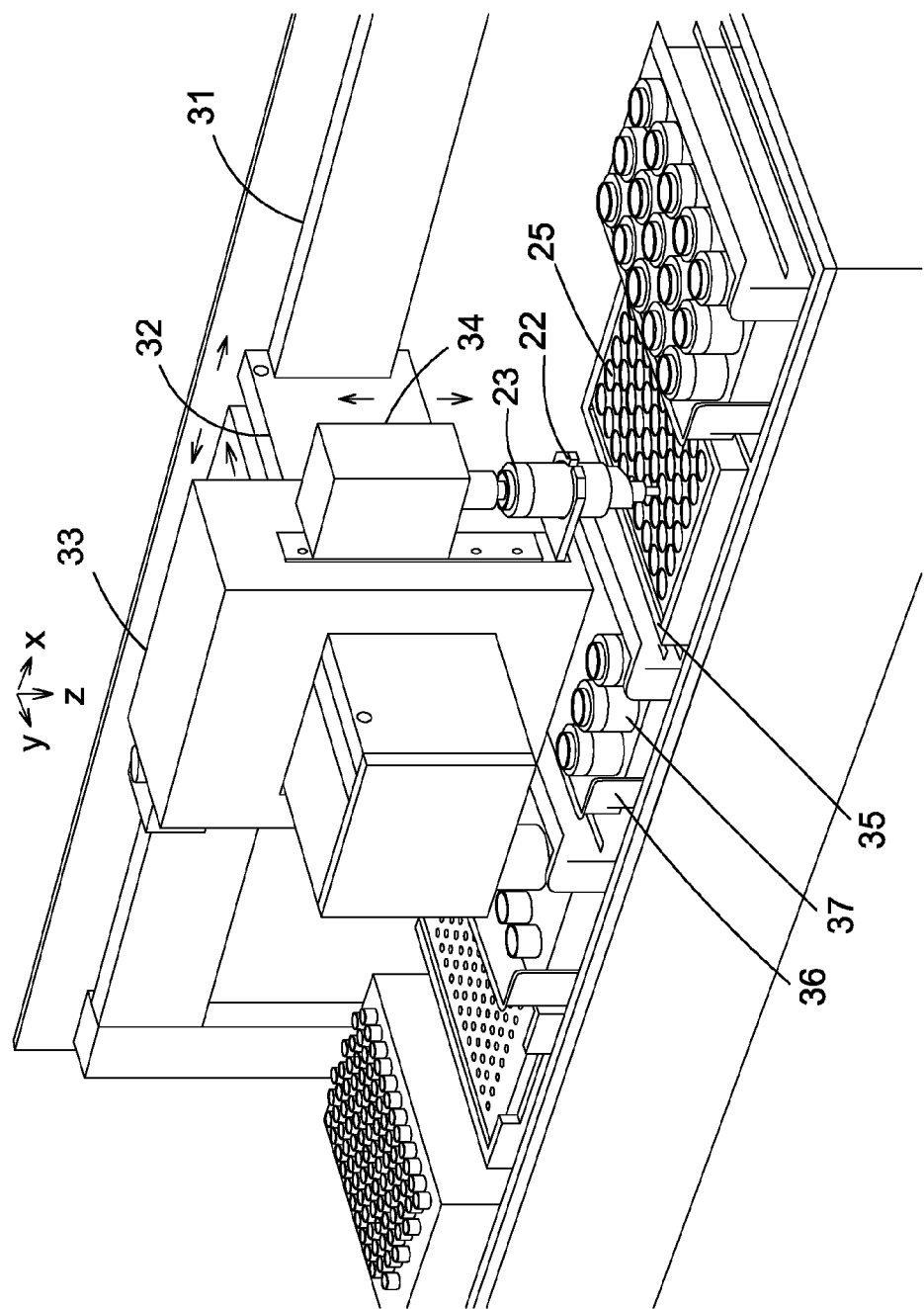
FIG. 5 shows a microarrayer comprising a reagent bead or microsphere syringe pick-up device mounted on an x-y-z translation stage and engaged with a reagent bead or microsphere dispenser above a sample plate.

A microarrayer or automated apparatus will now be described with reference to FIG. 5. As shown in FIG. 5, a plurality of syringe bodies 37 may be loaded onto a tray or pack 36 which can then be automatically loaded into the microarrayer or automated apparatus. The tray or pack 36 comprising a plurality of syringe bodies 37 may be moved by a three-axis translation mechanism or robotic arm to a reagent bead or microsphere dispensing work area of the microarrayer or automated apparatus.

The microarrayer or automated apparatus can comprise a three-axis translation mechanism which comprises a first translation stage comprising a guide rail 31 along which a first arm 32 may be translated in a first (x) horizontal direction. A second translation stage can be provided and comprises a mounting block 33 which encompasses or surrounds the first arm 32. The mounting block 33 may be translated in a second (y) horizontal direction (which is preferably orthogonal to the first (x) horizontal direction) and may be moved backwards and forwards along the first arm 32. A third translation stage can be provided and can comprise a body or syringe drive mechanism 34 which houses a linear actuator (not shown). The body or syringe drive mechanism 34 can be slidably mounted on the mounting block 33 and may be raised and lowered in a vertical (z) direction.

The three-axis translation mechanism can further comprise a retractable arm 35 which extends from the mounting block 33. The three-axis translation mechanism can be programmed to select and pick up a reagent bead or microsphere dispenser 22,37 from the tray or pack 36 comprising a plurality of reagent bead or microsphere dispensers 22,37. The body or syringe drive mechanism 34 comprises a tapered spigot which is resiliently mounted within a tubular housing. The spigot is arranged to engage with a tapered portion provided on the syringe cap 23 of the reagent bead or microsphere dispenser 22,37. When a reagent bead or microsphere dispenser 22,37 is positioned in the tray or pack 36 the spigot may be lowered onto the syringe cap 23 of a reagent bead or microsphere dispenser 22,37 thereby securing the reagent bead or microsphere dispenser 22,37 to the body or syringe drive mechanism 34 in a detachable manner. The body or syringe drive mechanism 34 and attached reagent bead or microsphere dispenser 22,37 may then be raised to a height such that the retractable arm 35 (which is initially retracted within the body of the mounting block 33) can then be extended. The reagent bead or microsphere dispenser 22,37 is then lowered by the body or syringe drive mechanism 34 so that the upper portion of the syringe body 24 is secured by the retractable arm 35. The retractable arm 35 can have an aperture having an internal diameter which is preferably smaller than the outermost diameter of a rim of the upper portion of the syringe body 24.

According to an embodiment each reagent bead or microsphere dispenser 22,37 comprises a plurality of identical reagent beads or microspheres. According to an embodiment up to 15 separate reagent bead or microsphere dispensers 22,37 may be loaded or provided in a single tray or pack 36 and each of the reagent bead or microsphere dispensers 22,37 may have a capacity of up to approximately 2000 reagent beads or microspheres.

According to an embodiment the syringe drive mechanism 34 is arranged to pick a reagent bead or microsphere dispenser 22,37 out of the tray or pack 36 and will position and lower the barrel 25 of the reagent bead or microsphere dispenser 22,37 so that it is immediately above a desired reagent bead or microsphere pocket or recess 21 provided in a sample well 19 of a sample plate. The syringe drive mechanism 34 is then actuated so that the actuator or plunger boss 28 of the reagent bead or microsphere dispenser 22,37 is depressed which in turn causes the plunger 27 to push a reagent bead or microsphere 20A from the chamber through the silicone member 30, through the barrel 25 and into the desired reagent bead or microsphere pocket or recess 21 of the sample well 19. The syringe drive mechanism 34 can be arranged to depress the actuator boss 28 and plunger 27 with a desired amount of force as opposed to moving the actuator or plunger boss 28 and plunger 27 to a certain vertical position. As a result, reagent beads or microspheres 20A are pressed in tightly and consistently into the reagent bead or microsphere pockets or recesses 21 of a sample well 19 with a constant amount of force.

Figure 6:
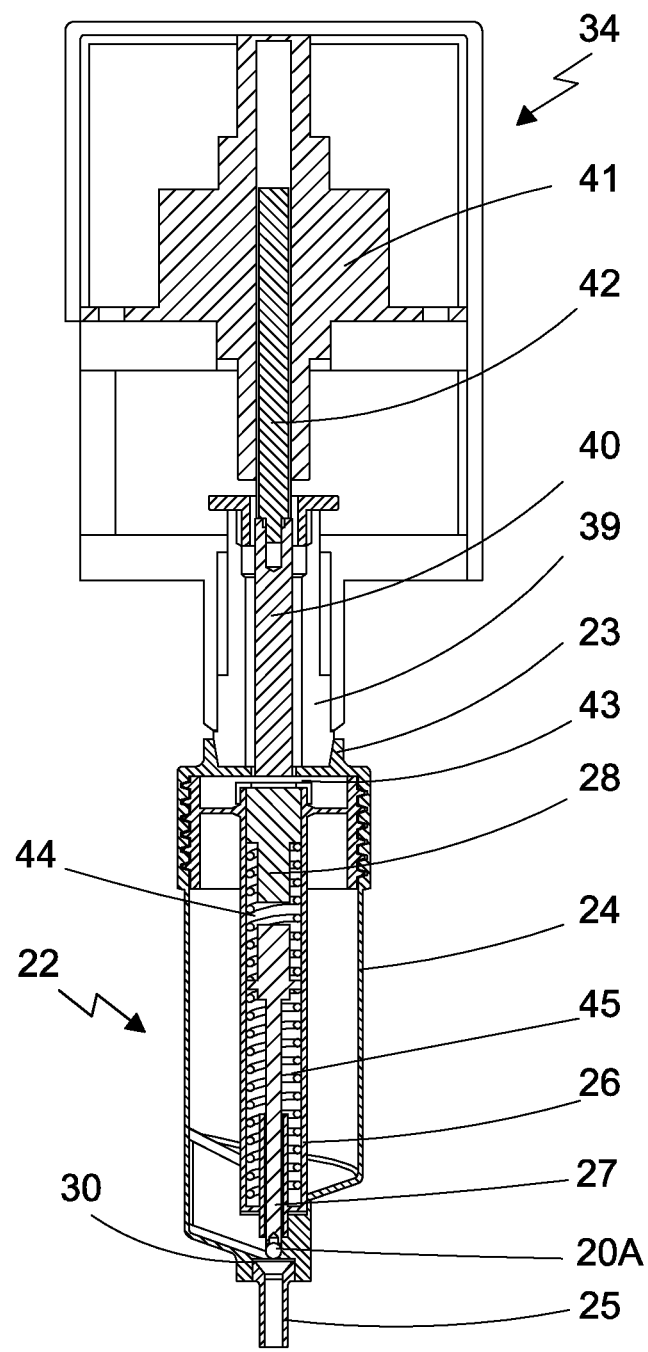
FIG. 6 shows in greater detail a cutaway view of a reagent bead or microsphere syringe pick-up device attached to a reagent bead or microsphere dispenser.

FIG. 6 shows in greater detail a reagent bead or microsphere dispenser pick-up device or syringe drive mechanism 34 during the process of picking up a reagent bead or microsphere dispenser 22. The reagent bead or microsphere dispenser pick-up device or syringe drive mechanism 34 comprises a spigot 39 having a tapered lower end which is arranged to engage with a tapered recess provided in the upper portion of the syringe cap 23 of the reagent bead or microsphere dispenser 22. The spigot 39 comprises a central bore through which a plunger push rod 40 is mounted. The plunger push rod 40 is arranged to be driven upwards or downwards by a linear actuator 41 which drives a linear actuator lead screw 42 which in turn raises or lowers the plunger push rod 40.

As shown in FIG. 6, in order to pick up a reagent bead or microsphere dispenser 22 the reagent bead or microsphere dispenser pick-up device or syringe drive mechanism 34 is lowered onto the reagent bead or microsphere dispenser 22 so that the spigot 39 of the reagent bead or microsphere pick-up device or syringe drive mechanism 34 engages with the syringe cap 23 of the reagent bead or microsphere dispenser 22. As the reagent bead or microsphere dispenser pick-up device or syringe drive mechanism 34 is driven downwards onto the reagent bead or microsphere dispenser 22, the spigot 39 becomes compressed and moves upwards until it is prevented from moving any further upwards. The spigot 39 can be driven further downwards whilst in a compressed state so that the interlocking tapers of the spigot 39 and syringe cap 23 engage causing the reagent bead or microsphere dispenser 22 to become attached to the reagent bead or microsphere pick-up device or syringe drive mechanism 34.

The reagent bead or microsphere dispenser 22 as shown in FIG. 6 is substantially similar to that shown in FIGS. 3A, 3B and 4 except that the spacer 29 shown in FIGS. 3B and 4 is replaced with a retaining cap 43 in the embodiment shown in FIG. 6. FIG. 6 also shows the location of an actuating spring 44 which is provided between the actuator or plunger boss 28 and the plunger 27 and which transmits force applied to the actuator or plunger boss 28 to the plunger 27. A return spring 45 is also shown and is provided between the plunger 27 and the base of the plunger guide 26 and causes the plunger 27 (and hence also the actuator or plunger boss 28) to return to an upper position when the actuator or plunger boss 28 is no longer depressed or actuated.

FIG. 7A shows the reagent bead or microsphere dispenser pick-up device or syringe drive mechanism 34 which has picked up a reagent bead or microsphere dispenser 22 and which is in the process of transporting the reagent bead or microsphere dispenser 22 to a desired location. Once the reagent bead or microsphere dispenser pick-up device or syringe drive mechanism 34 has engaged with the reagent bead or microsphere dispenser 22, the reagent bead or microsphere dispenser pick-up device or syringe drive mechanism 34 is raised so that the spigot 39 is no longer compressed. The spigot 39 returns to a downward position and the reagent bead or microsphere dispenser 22 including syringe body 24 is locked on to the spigot 39 by the tapers on the spigot 39 and syringe cap 23.

FIG. 7B shows a reagent bead or microsphere dispenser 22 in the process of dispensing a reagent bead or microsphere 20A from the reagent bead or microsphere dispenser 22 into a pocket or recess of a sample well (not shown) of a sample plate (not shown). The linear actuator 41 of the reagent bead or microsphere dispenser pick-up device or syringe drive mechanism 34 can be actuated and causes the linear actuator lead screw 42 to extend thereby pushing the push rod 40 downwards. The downwards movement of the push rod 40 depresses the actuator or plunger boss 28. The actuator or plunger boss 28 transmits force to the plunger 27 via the actuating spring 44 and in some embodiments, does not touch the plunger 27 directly. The plunger 27 forces a reagent bead or microsphere 20A from a chamber within the central bore provided within the syringe body 24. The reagent bead or microsphere 20A can be forced through the membrane 30 and down through the barrel 25 and into the recess or pocket of a sample plate (not shown) by the plunger 27.

FIG. 8A shows the reagent bead or microsphere pick-up device or syringe drive mechanism 34 in the process of ejecting a reagent bead or microsphere dispenser 22 from the end of the reagent bead or microsphere pick-up device or syringe drive mechanism 34. In this mode of operation the reagent bead or microsphere dispenser 22 is positioned above the tray or pack 36. The linear actuator 41 drives the linear actuator lead screw 42 downwards until the plunger 27 is extended a maximum extent. The spigot 39 is also extended to the maximum extent. The linear actuator 41 then continues to apply force via the actuator or plunger boss 28 to the plunger 27, as shown in FIG. 8B, with the result that the body of the reagent bead or microsphere dispenser 22 can be forced off from the end of the tapered spigot 39. The reagent bead or microsphere dispenser 22 then falls back into the reagent bead or microsphere dispenser tray or pack 36.

In order to illustrate aspects of an embodiment of the present invention a test was performed wherein a sample plate comprising nine sample wells 19 was provided. Each sample well 19 comprised ten pockets, recesses or bores 21 which were arranged in a circle around a central portion of the sample well 19. Each of the pockets, recesses or bores 21 were loaded with reagent beads or microspheres which were coated with different concentrations of reagent. The ten beads in the first sample well were coated with a reagent having a concentration of 10 μg/ml and the ten beads in the second sample well were coated with a reagent having a concentration of 8 μg/ml. The ten beads in the third sample well were coated with a reagent having a concentration of 4 μg/ml and the ten beads in the fourth sample well were coated with a reagent having a concentration of 2 μg/ml. The ten beads in the fifth sample well were coated with a reagent having a concentration of 1 μg/ml and the ten beads in the sixth sample well were coated with a reagent having a concentration of 0.5 μg/ml. The ten beads in the seventh sample well were not coated with a reagent i.e. the concentration was 0 μg/ml. The ten beads in the eighth sample well were coated with different concentrations of reagent and comprised concentrations of 10 μg/ml, 8 μg/ml, 4 μg/ml, 2 μg/ml, 1 μg/ml, 0.5 μg/ml, 0 μg/ml, 0 μg/ml, 0 μg/ml and 0 μg/ml. The ten beads in the ninth sample well had the same concentrations as the reagent beads or microspheres in the eighth sample well and were arranged in the same manner as the reagent beads or microspheres in the eighth sample well.

The reagent beads or microspheres were coated with a capture antibody comprising sheep IgG and were transported in a bicarbonate buffer containing 0.02% Kathon® preservative.

The sample wells 19 of the sample plate were emptied of the preservative in which the reagent beads or microspheres were transported in and 400 μl of a 1/1000 diluted donkey anti-sheep IgG peroxidise conjugate in a Tris Buffered Saline ("TBS") conjugate diluent buffer was added to each sample well 19. The sample plate was then incubated at ambient temperature and was subjected to medium intensity vibrations for a period of 45 minutes. Any unbound conjugate was then aspirated from the sample wells 19 using a single channel wash head of a microarrayer apparatus (DS2®, available from Dynex Technologies). Once any unbound conjugate had been aspirated from the sample wells 19, 500 μl of 1/20 diluted Tris Buffered Saline wash fluid was then immediately added to each sample well 19. The wash fluid was then aspirated from the sample wells 19 and the process of washing and aspirating wash fluid from the sample wells 19 was repeated twice more. After the third washing step including aspiration of wash fluid had been completed, 300 μl of luminol (a chemiluminescent marker) was then immediately added to each sample well 19. The sample plate was then incubated in the dark at ambient temperature whilst being subjected to medium intensity vibrations for 15 minutes. The sample plate was then transferred immediately to a reading chamber.

A camera was set to an exposure time of 6 minutes and 30 seconds with a gain of 20. Images were taken at 22 minutes and 29 minutes after luminol had been added. The camera exposure time was then changed to 8 minutes and 37 seconds. Further images were taken at 38 minutes, 47 minutes, 56 minutes and 65 minutes after luminol addition. Analysis of the images showed that the greatest observed signal strength was obtained after 15-22 minutes from luminol addition which is consistent with the luminol decay curve.

According to an embodiment the following steps may be carried out once reagent beads or microspheres have been dispensed into pockets, recesses or bores of a sample plate. Firstly, sample fluid may be added to one or more sample wells of the sample plate. The sample fluid may comprise one or more analytes such as specific antigens which may react with reagent coated on one or more of the reagent beads or microspheres. The reagent beads or microspheres can be coated with a specific capture antibody.

Once the sample fluid has been added to the sample wells, the sample plate can then be subjected to an incubation step. After the sample plate has been subjected to an incubation step so that antigen-antibody complexes are formed, the sample plate can then be subjected to one or more washing and aspirate steps in order to remove any unbound sample fluid and to remove any wash fluid. An enzyme conjugate can then added which will bind to the antigen part of any antigen-antibody complexes which have been formed but which will not bind to antibodies or to the antibody part of an antigen-antibody complex. The sample plate can then be incubated before being subjected to one or more washing and aspirate steps. Once the sample plate has been subjected to one or more washing and aspirate steps, luminol (or another visualizing agent) can be added. The sample plate is then aspirated to remove any excess luminol (or other visualizing agent). The luminol (or other visualizing agent) upon contacting enzymes attached to the antigen part of an antigen-antibody complex can then breakdown causing a distinctive color to be produced. In the final stage the sample plate is analyzed and an endpoint determination can be made.

Figure 9A:
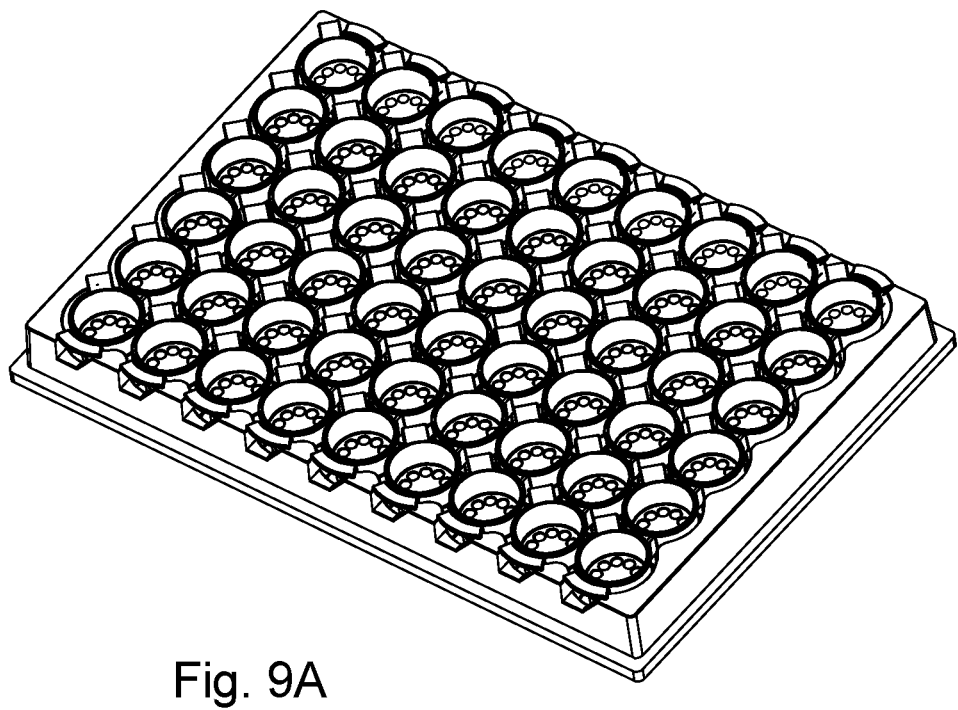
FIG. 9A shows nine sample strips loaded into a plate frame, wherein each sample strip comprises a 6×1 array of sample wells
Figure 9B:
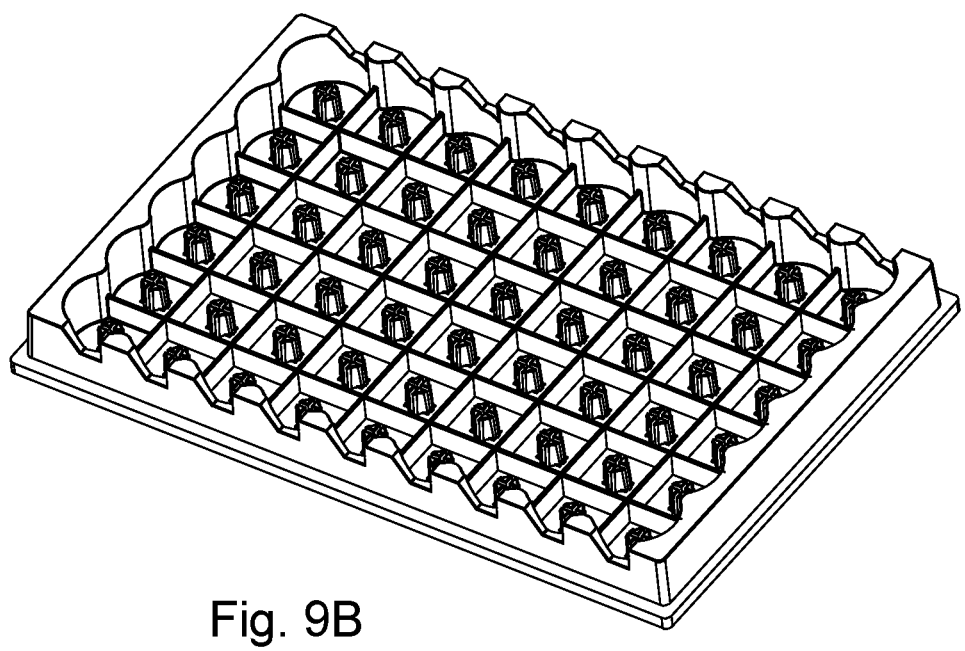
FIG. 9B shows a plate frame into which a sample plate or one or more sample strips may be loaded.

An embodiment is shown in FIGS. 9A and 9B and will be described in more detail below. FIG. 9A shows nine sample strips loaded into a plate frame. Each of the sample strips shown in FIG. 9A comprises a 6×1 strip of sample wells. The sample strips can be removeably loaded into the plate frame. Each of the nine sample strips comprises six sample wells and each sample well can comprise ten (optionally tapered) bores which, in use, are arranged to receive a reagent bead. The reagent beads can then be loaded or pre-loaded into the bores such that the reagent beads protrude above the base portion of the sample well. FIG. 9B shows the plate frame into which the sample plates may be loaded in more detail.

Figure 10A:
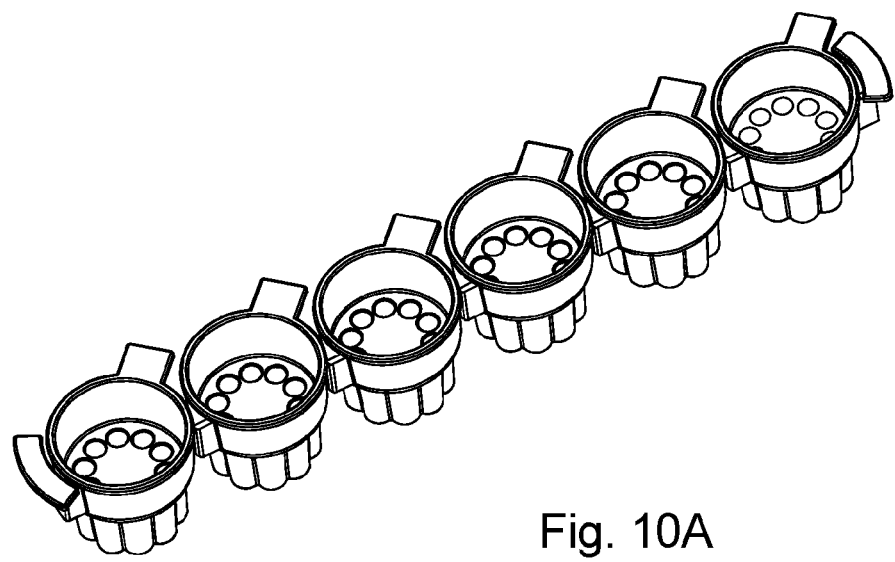
FIG. 10A shows in greater detail a sample strip comprising six sample wells and FIG. 10B shows a sample strip comprising six sample wells being loaded into a plate frame.
Figure 10B:
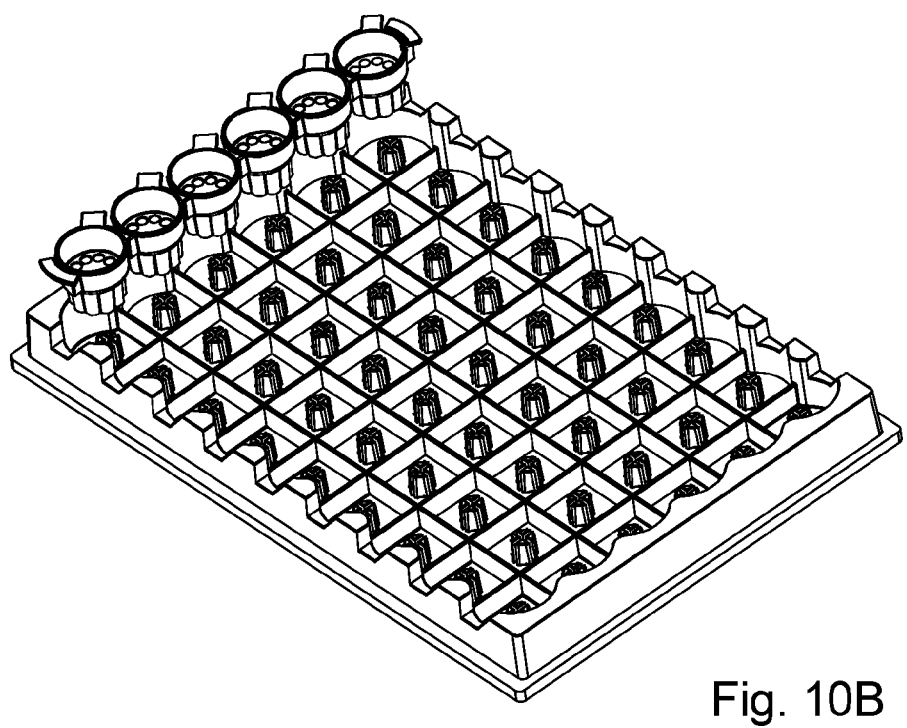

FIG. 10A shows in greater detail a sample strip comprising six sample wells. According to an embodiment the sample wells in a strip can be separated or otherwise broken apart. According to an embodiment the sample plate or strip can be separated or divided up into single sample wells. FIG. 10B shows a sample strip comprising six sample wells being loaded into a plate frame.

Figure 11A:
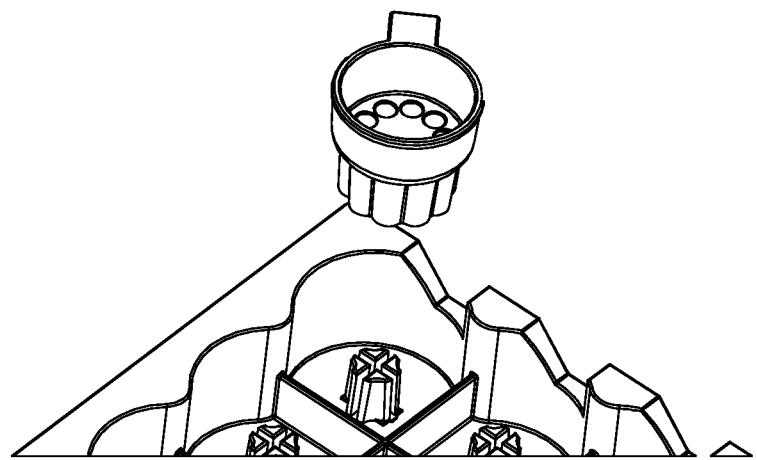
FIG. 11A shows a single well being loaded into a plate frame.

FIG. 11A shows a single sample well (which has been separated from a strip of sample wells) being loaded into a plate frame. The sample wells can comprise a female portion which is arranged to engage or interlock with a male portion which can be provided on the base of the plate frame. The sample plate or sample strip can be arranged to be firmly secured and fixed to the plate frame when loaded onto the plate frame.

Figure 11B:
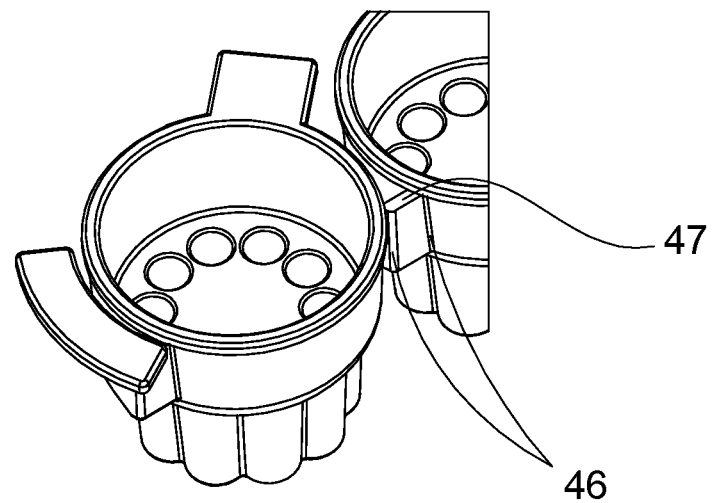
FIG. 11B shows in greater detail two sample wells connected by a break apart feature.

FIG. 11B shows in greater detail two sample wells which are connected by a break-apart feature 47. The break-apart feature 47 can allow a user to separate adjacent sample wells. According to an embodiment sample wells may be separated from each other but may still be placed next to each other on the plate frame without interfering with each other. The break-apart feature 47 can comprise one, two or more than two break points 46. According to an embodiment the connecting piece 47 between two sample wells may be separated from a sample well at a first break point 46. The connecting piece 47 may then be broken off or otherwise removed from the single sample well that it is attached to by breaking the connecting piece 47 from the sample well at a second break point 46.

Figure 11C:
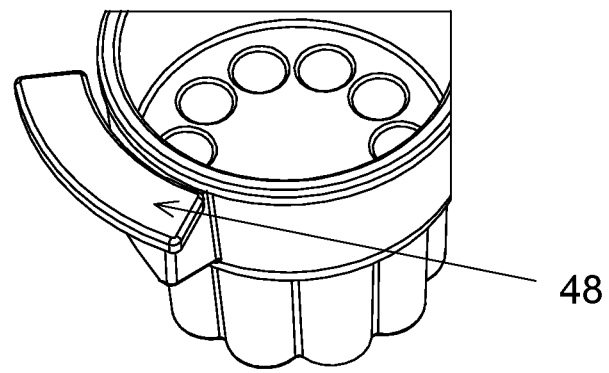
FIG. 11C shows a sample well having an end feature and FIG. 11D shows a sample well having an ID and orientation tab.

FIG. 11C shows a sample well having an end break-apart feature 48. The end break-apart feature 48 can allow the end wells to be used singly in the plate frame without interfering with another sample well. The end break-apart feature 48 provides something for a user to hold in order to remove a strip of sample wells or a single sample well from the plate frame.

Figure 11D:
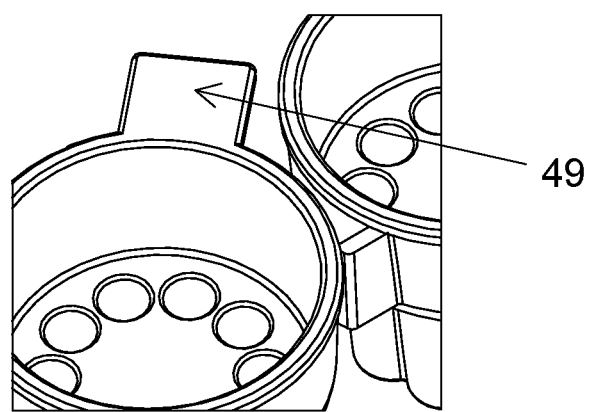

FIG. 11D shows a sample well having an ID and orientation tab 49. The tab 49 can allow an identifier to be printed onto the tab 49 or to be otherwise attached to the tab 49. The identifier may comprise a 2D or 3D barcode and/or human readable text. The tab 49 can assist a user to orientate a sample well when a single sample well is used by aligning with features in the plate frame and/or on other sample wells.

Figure 12A:
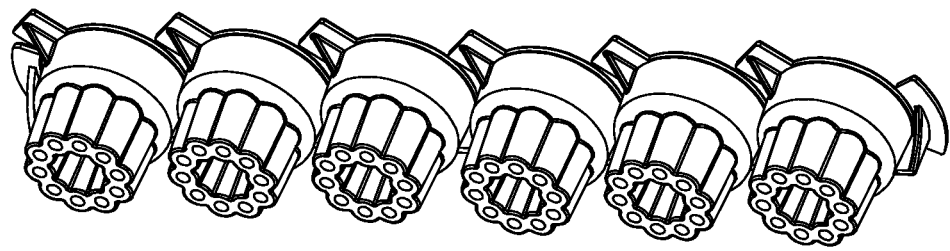
FIG. 12A shows the underneath of a strip of sample wells.

FIG. 12A shows the underneath of a strip of sample wells and shows that according to an embodiment each sample well comprises ten bores or recesses in which a reagent bead can be inserted in use. The base or underside of each sample well can also comprise a female portion which can be arranged to be mated, in use, with a male portion which can be provided in the base of the plate frame.

Figure 12B:
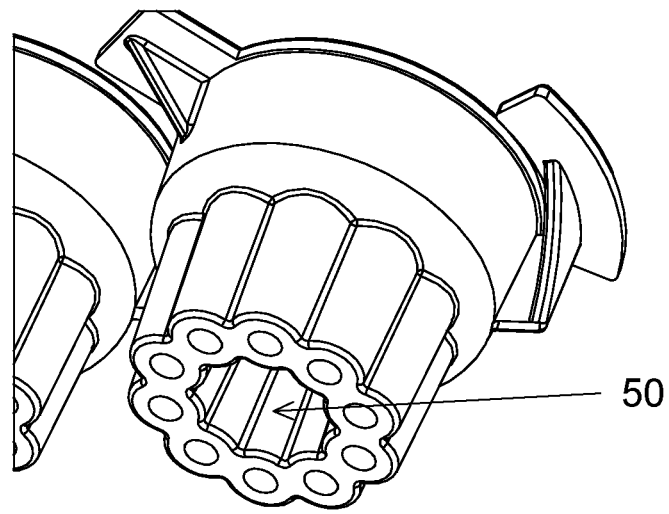
FIG. 12B shows a female alignment and retaining feature which helps to align a sample strip or sample well with a plate frame and FIG. 12C shows a corresponding male alignment and retaining feature which is provided in the base of the plate frame.
Figure 12C:
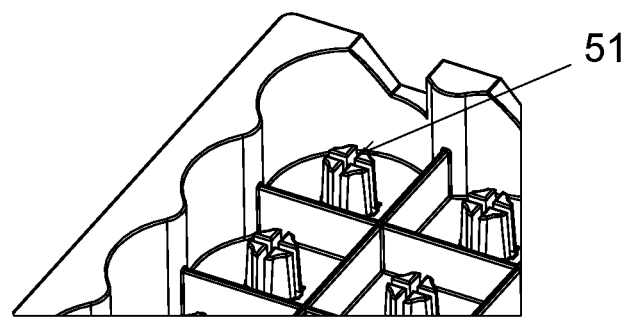

FIG. 12B shows in greater detail a female alignment and retaining feature 50 which helps to align a strip of sample wells with a plate frame. FIG. 12C shows a corresponding male alignment and retaining feature 51 which can be provided in the base of the plate frame. The male portion 51 may according to an embodiment comprise a plurality of flexible projections which are preferably deformed inwards as a sample well is located over the male portion 51. The projections on the plate frame can move or close together ensuring that the sample well is kept in place without having to apply undue force either to mount or fix a sample well onto the plate frame and/or to demount a sample well from the plate frame.

Figure 13:
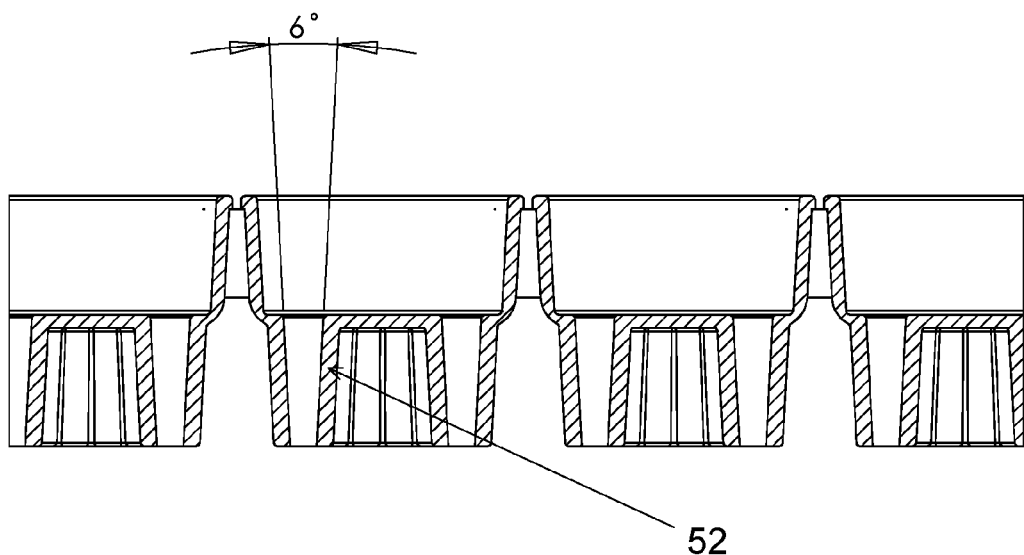
FIG. 13 shows a cross-sectional view of a strip of sample wells and shows an embodiment wherein the sample wells have a plurality of tapered bores wherein the angle of the taper is 6.0°.

FIG. 13 shows a cross-sectional view of a strip of sample wells and shows that according to an embodiment the sample wells may comprise a plurality of tapered bores 52. The tapered bores 52 preferably act as pockets into which a reagent bead is inserted in use. The angle of the taper in the embodiment shown in FIG. 13 is 6.0°.

Although various embodiments described above have focused upon reagent beads which are coated with a biomolecule for use in an Immunoassay or ELISA procedure, other embodiments equally apply to reagent beads which comprise or which are otherwise coated with a nucleic acid sequence and which are used as a hybridization probe for the detection of DNA or RNA sequences which are complementary to those provided on the reagent beads. In some embodiments, the hybridization probe will be inactive until hybridization, at which point there is a conformational change and the molecule complex becomes active and will then fluoresce under UV light. Therefore, all the various embodiments described above and all the various aspects of the embodiments described above apply equally to the use of reagent beads comprising or which are otherwise coated with a DNA or RNA sequence (or other nucleotide sequence) for use as a hybridization probe to detect complementary DNA or RNA sequences.

Many variants, including fluorogenic and luminogenic substrates for ELISA, direct labeling of the second member of the binding pair with a fluorescent or luminescent molecule (in which case the procedure is not called an ELISA but the process steps are very similar) and nucleic acids or other specific pairing agents instead of antibodies can be used as a probe. The same principles can be used to detect or determine any materials which can form specific binding pairs, for example using lectins, rheumatoid factor, protein A or nucleic acids as one of the binding partners.

The sample plate can thus be used to detect an analyte, such as a biomarker, which can be indicative of a disease or condition. The disease or condition can be a tumor, neoplasm, or cancer, such as breast cancer, ovarian cancer, lung cancer, colon cancer, hyperplastic polyp, adenoma, colorectal cancer, high grade dysplasia, low grade dysplasia, prostatic hyperplasia, prostate cancer, melanoma, pancreatic cancer, brain cancer (such as a glioblastoma), hematological malignancy, hepatocellular carcinoma, cervical cancer, endometrial cancer, head and neck cancer, esophageal cancer, gastrointestinal stromal tumor (GIST), renal cell carcinoma (RCC) or gastric cancer. The disease or condition can also be an inflammatory disease, immune disease, or autoimmune disease, such as inflammatory bowel disease (IBD), Crohn's disease (CD), ulcerative colitis (UC), pelvic inflammation, vasculitis, psoriasis, diabetes, autoimmune hepatitis, Multiple Sclerosis, Myasthenia Gravis, Type I diabetes, Rheumatoid Arthritis, Psoriasis, Systemic Lupus Erythematosis (SLE), Hashimoto's Thyroiditis, Grave's disease, Ankylosing Spondylitis Sjogrens Disease, CREST syndrome, Scleroderma, Rheumatic Disease, organ rejection, Primary Sclerosing Cholangitis, or sepsis. The disease or condition can also be a cardiovascular disease, such as atherosclerosis, congestive heart failure, vulnerable plaque, stroke, ischemia, high blood pressure, stenosis, vessel occlusion or a thrombotic event. The disease or condition can also be a neurological disease, such as Multiple Sclerosis (MS), Parkinson's Disease (PD), Alzheimer's Disease (AD), schizophrenia, bipolar disorder, depression, autism, Prion Disease, Pick's disease, dementia, Huntington disease (HD), Down's syndrome, cerebrovascular disease, Rasmussen's encephalitis, viral meningitis, neurospsychiatric systemic lupus erythematosus (NPSLE), amyotrophic lateral sclerosis, Creutzfeldt-Jacob disease, Gerstmann-Straussler-Scheinker disease, transmissible spongiform encephalopathy, ischemic reperfusion damage (e.g. stroke), brain trauma, microbial infection, or chronic fatigue syndrome. The phenotype may also be a condition such as fibromyalgia, chronic neuropathic pain, or peripheral neuropathic pain. The disease or condition can also be an infectious disease, such as a bacterial, viral or yeast infection. For example, the disease or condition may be Whipple's Disease, Prion Disease, cirrhosis, methicillin-resistant staphylococcus aureus, HIV, hepatitis, syphilis, meningitis, malaria, tuberculosis, or influenza. Viral proteins, such as HIV or HCV-like particles can be assessed in an exosome, to characterize a viral condition.

The sample plate can be used to detect a biomarker that is used to detect the disease or condition. For example, the detection of a biomarker can be used to detect or provide a diagnosis, prognosis of a disease or condition. For example, the sample plate can comprise a probe for a cancer marker, and used to detect the cancer marker in a sample from an individual. The presence, absence, or level of the cancer marker in the sample can be indicative of cancer in the individual. In another embodiment, the sample plate can also be used to monitor a disease or condition. For example, an increased level of the cancer marker, as compared to a control, or compared to an earlier assay for the cancer marker from the same individual, can be indicative of progression of the cancer. In yet another embodiment, the sample plate can be used to in determine a therapy or course of action for a condition. For example, an individual may have a genetic variant which leads to the individual being unable to metabolize certain drugs. The sample plate can be used to detect the genetic variant. In another embodiment, the sample plate may be used to detect a compound, which can be indicative of a drug not being metabolized. The sample plate can also be used to detect the intake of certain drugs or compounds, such as be detecting the drug or by-products of the drug, which can be used for drug testing.

The sample plate can also be used to screen for drugs. For example, the sample plate can comprise a probe that is a target for drug development. The sample plate can then be used to screen a library of compounds. Alternatively, the sample plate can comprise a plurality of probes that comprise a library of compounds that are potential drugs. The sample can comprise a drug target, which is added to the sample plate.

Also provided herein is a kit comprising a sample plate disclosed herein. The kit can comprise one or more components for detecting an analyte or for performing an assay. In one embodiment, a kit for detecting an analyte comprises one or more sample plates and a plurality of beads. The plurality of beads can comprise one or more probes, such as a probe that is a nucleic acid, antibody, antibody fragment, protein, peptide, aptamer, or chemical compound. In another embodiment, a kit for performing an Enzyme Linked Immunosorbent Assay (ELISA) procedure is provided. The kit can comprise one or more sample plates as described herein; and a plurality of beads, wherein the beads are coated with a reagent comprising an antibody, an antigen or another biomolecule. In yet another embodiment, the kit can comprise components for performing a nucleic acid probe procedure, wherein the kit comprises one or more sample plates as described herein; and a plurality of beads coated with a nucleic acid, such as a DNA or RNA probe or sequence.

Figure 14A:
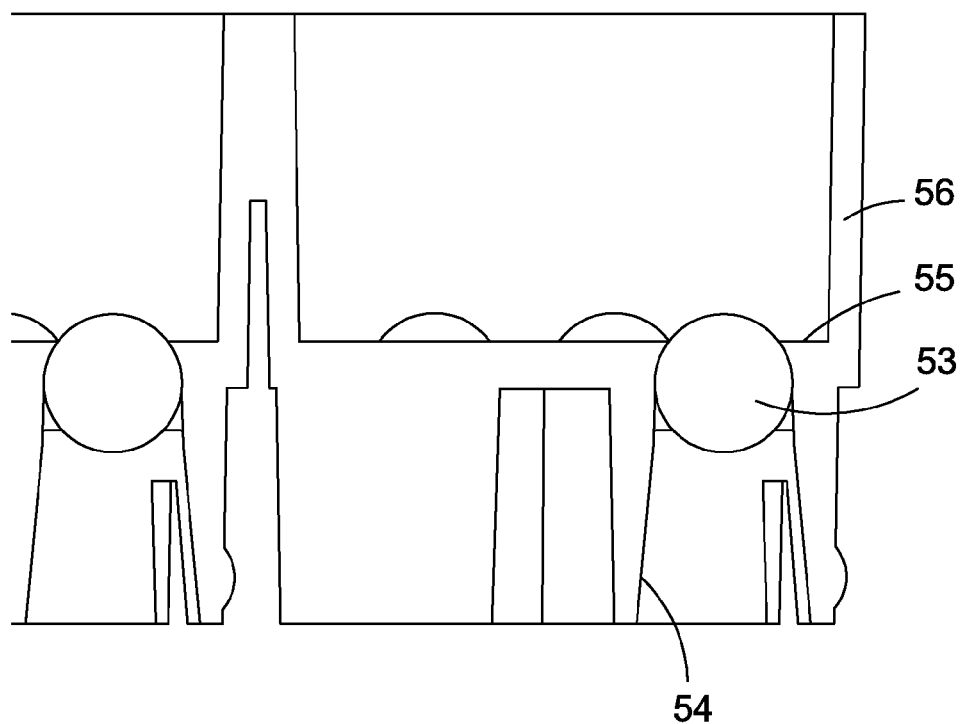
FIG. 14A shows a further embodiment of the present invention wherein conical through holes are provided in the base portion of a sample plate and reagent beads are loaded from the rear of the sample plate and FIG. 14B shows a sample plate according to a preferred embodiment wherein the sample plate has a cylindrical non-tapered through hole such that reagent beads may be loaded or inserted from the top through the sample well and are secured within the through hole by an interference fit.
Figure 14B:
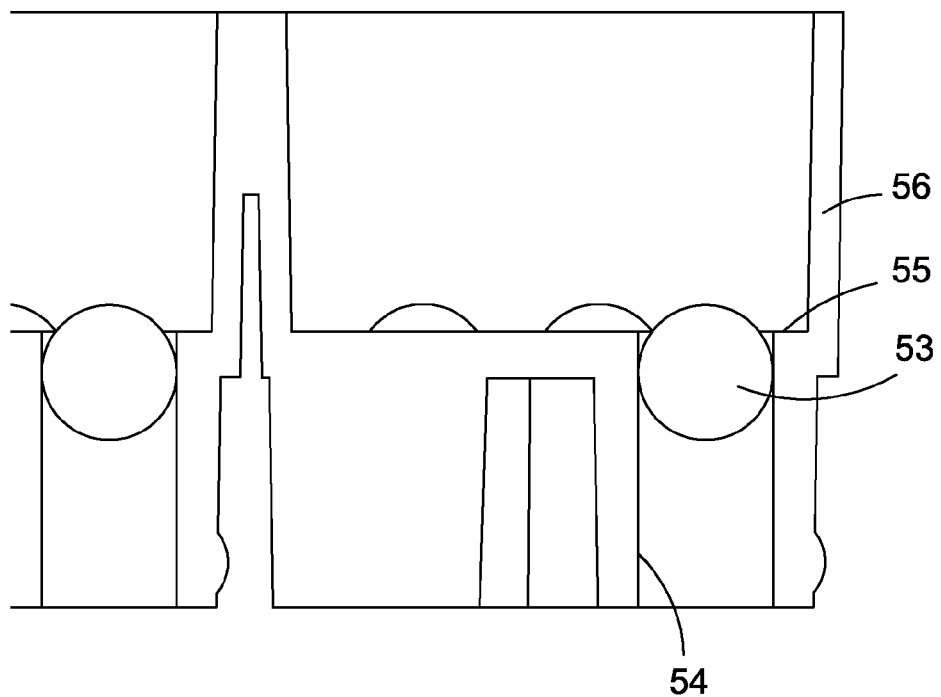

Further embodiments of the present invention will now be described with reference to FIGS. 14A and 14B. According to the embodiment shown in FIG. 14A reagent beads 53 are loaded into a sample plate from the underneath or rear side of the sample plate. The sample plate comprises a bore or through hole 54 which according to the embodiment as shown in FIG. 14A is tapered. However, as will be discussed below, it is also contemplated that the bore or through hole may not be tapered and may instead comprise a substantially cylindrical through hole or bore 54 which has a substantially constant cross-sectional diameter and/or area and/or profile. FIG. 14B shows a sample plate according to an embodiment of the present invention wherein reagent beads or microspheres are secured within a cylindrical bore or through hole 54. The reagent beads or microspheres may be inserted into the cylindrical bore or through hole 54 either from the top or from the bottom. The reagent beads or microspheres can be secured within the bore or through hole 54 by an interference fit and the reagent beads or microspheres make a substantially fluid-tight seal around a full circumference of, perimeter of or closed loop around the reagent bead or microsphere.

Figure 15:
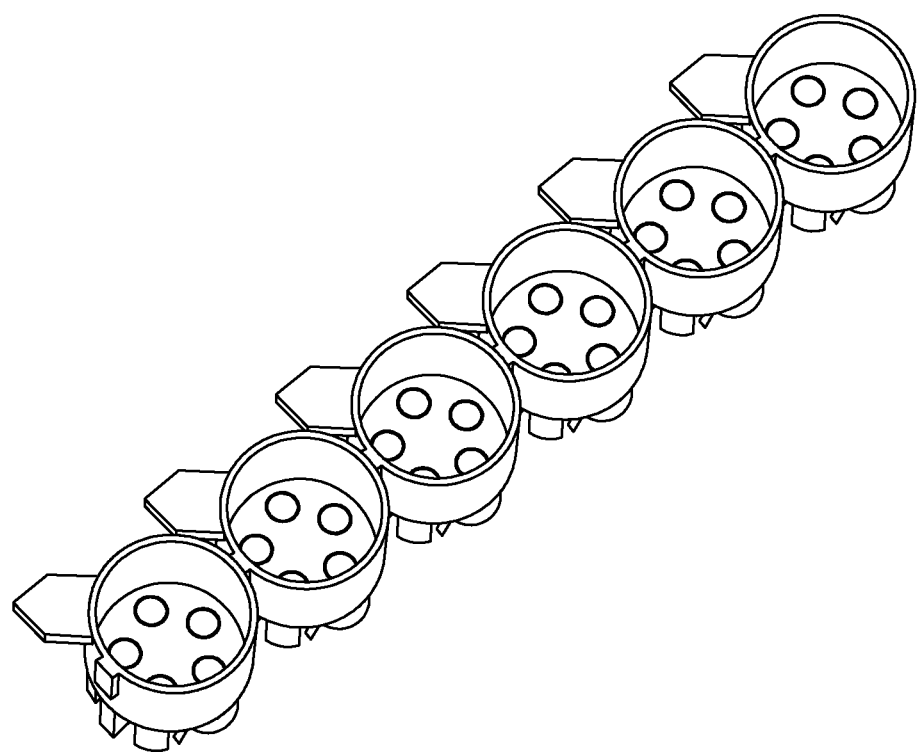
FIG. 15 shows a sample strip comprising six sample wells wherein reagent beads are fitted from the underneath of the sample plate.

With regard to the embodiment shown in FIG. 15 and referring back to FIG. 14A, bores or through holes 54 in a sample well may taper from a first diameter at the lowermost part or bottom of the base portion 55 of the sample well 56 to a second narrower diameter towards the uppermost part or top of the base portion 55. The uppermost part or top of the base portion 55 is that part of the base portion 55 which comes into contact with sample fluid in use.

At the top of the bore or through hole 54 immediately below the portion of the base portion 55 which comes into contact with sample fluid, the bore or through hole 54 may be shaped so as to form a tight fit with a reagent bead 53. The uppermost portion of the bore or through hole may comprise a part spherical profile, bulbous region, curved portion or concave region so that a reagent bead 53 which is inserted into the bore or through hole 54 from the underneath of the sample plate fits tightly within the part spherical profile, bulbous region, curved portion or concave region at the top of the bore or through hole 54 as shown in FIG. 14A.

According to an embodiment at least a portion of the reagent bead 53 is arranged to project into the base or bottom of the sample well to form, in effect, part of the base portion of the sample well 56. As a result, the top portion of the reagent bead 53 (above the region where the bead forms a fluid-tight circumferential seal with the wall of the through hole) is arranged so as to come into contact with sample fluid in use. The reagent bead 53 forms a fluid tight seal around the full circumference of the bead 53 with the part spherical profile, bulbous region, curved portion or concave region of the bore or through hole 54.

According to an embodiment macro sized beads 53 are fitted into a sample well 56 of a sample plate so that only the top or upper portion of the reagent bead 53 is exposed to fluid. It should be noted that the luminescent reading process is a 2D operation and only takes into account signal from the visible portion of the reagent bead 53 facing the camera.

According to an embodiment the multiplex well together with reagent beads loaded into the through holes preferably mimics the well established microplate ELISA type of process. The multiplex well according to an embodiment is substantially similar in format to a microplate well.

One of the major factors in processing an ELISA test in a microplate is the efficiency or cleanliness of each step. Any residual fluid from the steps can have an overall effect on the performance of the test e.g. if the conjugate is not completely removed by washing, then residual conjugate will produce a false signal on the bead. This will drive down the sensitivity of the test by increasing the background signal.

One aspect of efficient processing of the test is not to have any fluid traps in the well. Any corners, pockets or undercuts may trap fluid thereby reducing the performance of the sample plate. The sample plate according to an embodiment can allow efficient washing, mixing and aspirating in a similar manner to a conventional microplate well and in some embodiments does not suffer from the problem of trapping fluid.

In some embodiments beads 53 can be fitted at a uniform height in a sample well 56 which can ensure that each bead 53 is treated identically. Each bead 53 makes a fluid tight sealed fit in the locating detail of a pocket of through hole to ensure that there is no fluid trapped under or below the bead 53.

The through hole 54 may comprise a tapered conical hole in which the bead locks into the hole as shown in FIG. 14A or the through hole 54 may comprise a cylindrical undersized hole into which a bead is mechanically pressed into as shown in FIG. 14B. Both embodiments can achieve the goal of preventing fluid going past the bead 53 and becoming trapped underneath or below the bead 53.

If the sample plate comprises one or more tapered through holes 54 as shown in FIG. 14A then the through holes can be manufactured with a high degree of accuracy and consistency to ensure that beads are secured within the sample plate at a uniform height (since the reagent beads 53 can be pressed into the through holes 54 with a set force and not to a set height). The alternative embodiment of using undersized cylindrical through holes as shown in FIG. 14B may not need to be manufactured to so such a high degree of accuracy since the reagent beads 53 can be pressed in to the through holes to a set height and not with a set force.

In some of the embodiments described above reagent beads may be fitted into a blind pocket detail in a sample well i.e. into a closed recess. However, in some embodiments, a sample plate having through holes in the base portion may be provided as shown and described above with reference to FIGS. 14A and 14B.

The assembly of a sample plate which is loaded with reagent beads during production or manufacture can be subjected to a quality control check to ensure that all the beads are sealed to the sample plate. Beads which are loaded into blind pockets as described above can ensure that fluid will not leak out of the well. However, fluid might still leak under the bead and such a leak would be difficult to detect.

According to an embodiment, a sample plate comprising through holes as shown in FIGS. 14A and 14B can allow a pressure check to be carried out as part of the bead to plate assembly, manufacture and quality control checks. This can ensure that the bead to plate seal is good. A defective bead or damaged hole would show up as a fail in the manufacture and not when the user runs the test.

The sample plate according to the embodiments as shown in FIG. 14A or optionally also in FIG. 14B wherein reagent beads are fitted into the bore from underneath can be particularly advantageous for a number of reasons. Firstly, contact between a press in tool and the bead 53 is with the bottom or underneath portion of the reagent bead 53 so any witness mark can also be on the bottom or underneath portion of the reagent bead 53 i.e. not any portion of the reagent bead 53 which will come into contact with sample fluid. Secondly, the top of the through hole 53 in the base portion 55 of the sample well in the example shown in FIG. 14A can be made to match the profile or shape of the reagent bead 53 so that no moat portion is formed around the portion of the bead 53 which protrudes into the base of the sample plate. As a result, the design can minimize or exclude any possibility of trapping fluid below the reagent bead 53. Thirdly, it can minimize or eliminate cross contamination between beads since the press in tool will only come into contact with the underneath or bottom portion of the reagent beads 53—the press in tool does not come into contact with the top portion of the reagent beads 53 (i.e. the portion of the reagent beads 53 which will come into contact with sample fluid). Fourthly, in the embodiment shown in FIG. 14A reagent beads 53 can be fitted lower in the base portion without forming a moat region and in a manner which reduces the risk of crosstalk.

According to an embodiment fluid is only arranged to come into contact with the top surface of a reagent bead 53. According to an embodiment fluid is prevented from passing down a through hole 54 or recess past a reagent bead 53 secured within the through hole 54 or recess.

A sample plate according to an embodiment can be cleaned easily during the process steps without trapping fluid under the reagent beads 53. The beads 53 can be provided in a format that makes it as close to a cylindrical well as possible and which can also be easily accessed from the top.

FIG. 15 shows an embodiment wherein a strip of six sample wells with five 3 mm reagent beads loaded into through holes in each sample well. The reagent beads can be loaded into the through holes from the bottom or underneath of the sample plate. The reagent beads can be retained within the through holes by upper concave regions formed in the through holes.

Figure 16:
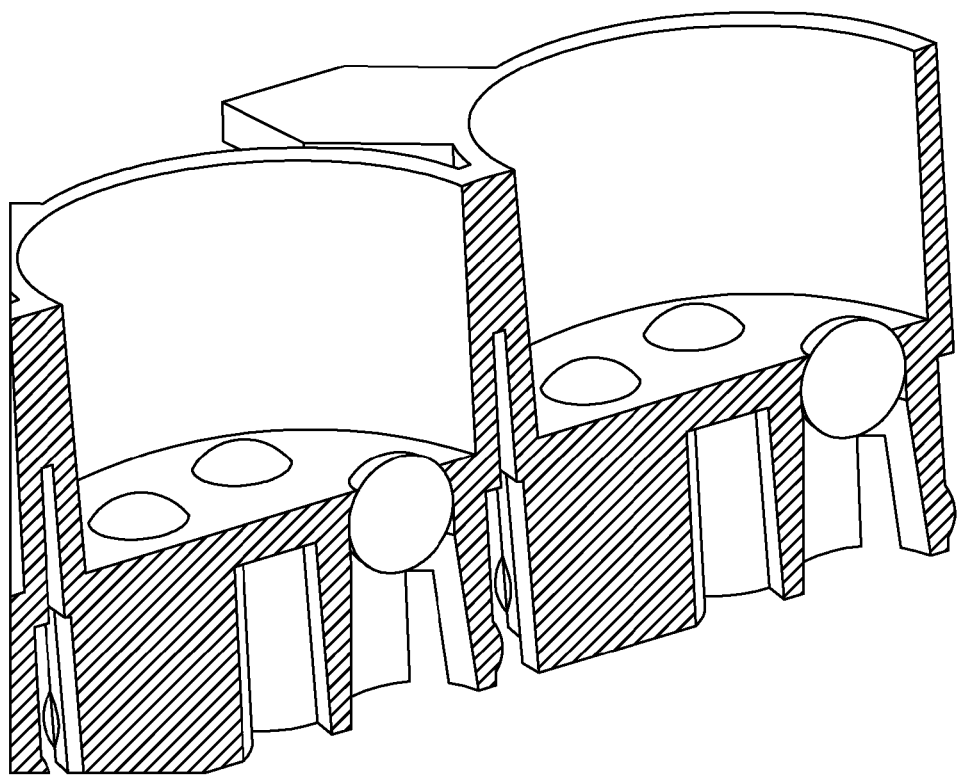
FIG. 16 shows a cross sectional 3D view of the further embodiment showing reagent beads located within a concave end portion of a through hole.

FIG. 16 shows a three dimensional cross-sectional view of the arrangement as shown and described above with reference to FIGS. 14A and 15.

Figure 17:
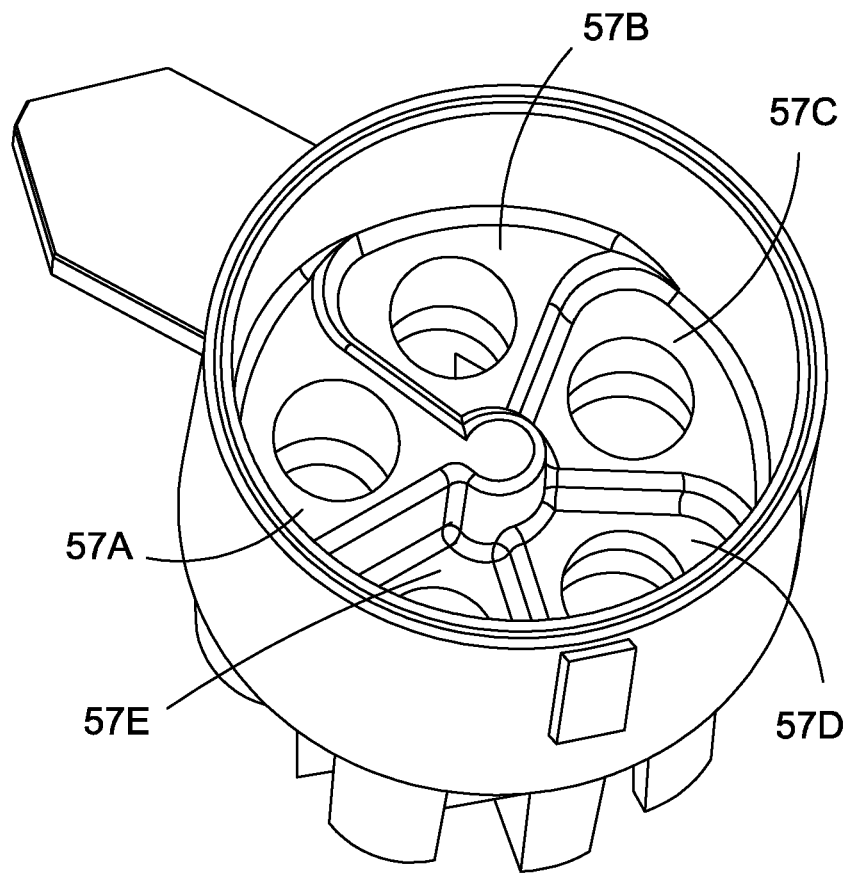
FIG. 17 shows an embodiment wherein the base portion of a sample well is segmented into five segments and each base portion segment is arranged at a different relative height so that there is no direct line of sight between reagent beads inserted into open through holes or recesses provided in each base portion segment.

FIG. 17 shows a further embodiment of the present invention wherein the base portion of a sample well is sub-divided into a plurality of segments 57A-E. According to an embodiment each base portion segment 57A-E has one or more open through holes provided in the base portion segment so that a reagent bead can be inserted from above or below into the open through hole. According to another embodiment each base portion segment 57A-E may have one or more blind recesses provided in the base portion segment so that a reagent bead can be inserted from above into the blind recess. According to another embodiment some of the base portion segments 57A-E may comprise one or more through holes and other base portion segments 57A-E may comprise one or more blind recesses. According to an embodiment some or all of the through holes and/or recesses are non-tapered and comprise a cylindrical bore. However, according to another embodiment some or all of the through holes and/or some or all of the recesses may be tapered.

According to an embodiment reagent beads or microspheres are retained or secured, in use, within the through holes and/or recesses provided in the base portion segments so as to form a substantially fluid-tight circumferential seal with a wall of the base portion segment which defines the through hole and/or the recess.

The base portion segments 57A-E may be arranged in a spiral or other staggered arrangement in a similar manner to that shown in FIG. 17. The base portion segments 57A-E can be arranged at different relative heights to each another so that once reagent beads have been inserted into the open through holes or recesses provided in the base portion segments 57A-E then there is no direct line of sight between adjacent reagent beads (or any line of sight between adjacent reagent beads is significantly reduced). In the embodiment shown in FIG. 17, base portion segment 57A is relatively higher than base portion segment 57B; base portion segment 57B is relatively higher than base portion segment 57C; base portion segment 57C is relatively higher than base portion segment 57D; and base portion segment 57D is relatively higher than base portion segment 57E. Embodiments wherein there is no (or alternatively, a reduced) direct line of sight between reagent beads inserted into through holes and/or recesses in base portion segments provided within the same sample well (including the embodiment shown and described above with reference to FIG. 17) can reduce or eliminate crosstalk between reagent beads when the reagent beads are subsequently optically analyzed to determine the intensity of a reaction. According to an embodiment the reagent beads include an indicator which during an analysis step is illuminated by a light source and the intensity of the indicator on a reagent bead is determined by a detector such as a camera to give a measure of the intensity of a reaction.

Figure 18A:
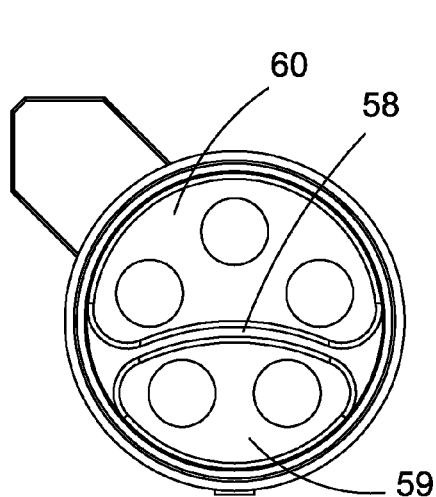
FIG. 18A shows a plan view of an embodiment wherein a relatively low-height baffle divides a base portion into two sections so that there is no direct line of sight between reagent beads inserted into open through holes or recesses provided in one section and reagent beads inserted into open through holes or recesses provided in the other section and FIG. 18B shows a 3D view of an embodiment wherein a low-height baffle separates the base portion into two sections so that there is no direct line of sight between reagent beads inserted into open through holes or recesses provided in one section and reagent beads inserted into open through holes or recesses provided in the other section.
Figure 18B:
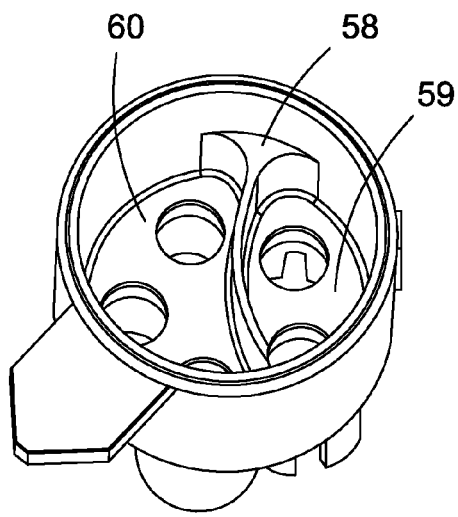

FIGS. 18A and 18B show another embodiment wherein a low-height baffle 58 is provided in a sample well so as to sub-divide the base portion of the sample well into a first base portion 59 having two open through holes or recesses and a second base portion 60 having three open through holes or recesses. It will be understood that other embodiments are contemplated wherein the first base portion 59 and/or the second base portion 60 may comprise a greater or lesser number of open through holes or recesses.

Figure 19A:
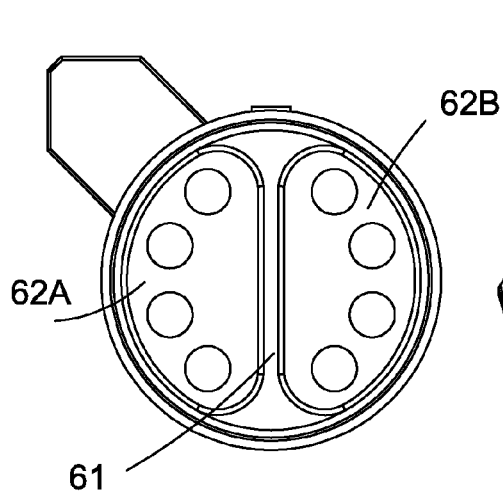
FIG. 19A shows a plan view of an embodiment wherein a relatively low-height baffle divides a base portion into two sections so that there is no direct line of sight between reagent beads inserted into open through holes or recesses provided in one section and reagent beads inserted into open through holes or recesses provided in the other section and FIG. 19B shows a 3D view of an embodiment wherein a relatively low-height baffle divides a base portion into two sections so that there is no direct line of sight between reagent beads inserted into open through holes or recesses provided in one section and reagent beads inserted into open through holes or recesses provided in the other section.
Figure 19B:
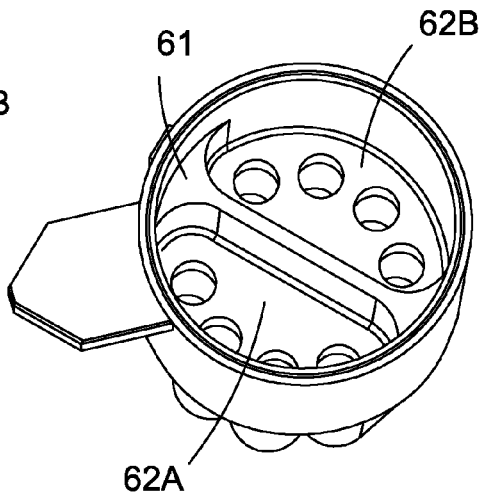

FIGS. 19A and 19B show another embodiment wherein a low-height baffle 61 is provided in the sample well. According to the particular embodiment shown in FIGS. 19A and 19B, the baffle 61 sub-divides the base portion of the sample well into a first base portion 62A having four open through holes or recesses and a second base portion 62B also having four open through holes or recesses.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A sample plate comprising one or more sample wells, wherein one or more of said sample wells comprise:
    (a) a base portion; and
    (b) two or more recesses provided in said base portion; wherein each of said two or more recesses has a dimension and contains a bead deposited in said well to be substantially retained or secured within said recess, and said bead forms a substantially fluid-tight circumferential seal with a wall of said base portion which defines said recess.

2. The sample plate of claim 1, wherein each of said two or more recesses comprise a blind recess or an open through hole.

3. The sample plate of claim 1, wherein said recess is substantially cylindrical.

4. The sample plate of claim 1, wherein an opening to said recess is circular.

5. The sample plate of claim 1, wherein said recess is conical and has a first diameter which is greater than a diameter of a bead deposited in said recess and a second diameter which is less than a diameter of said bead deposited in said recess.

6. The sample plate of claim 5, wherein said through recess has a taper selected from the group consisting of: (i)<0.5.degree.; (ii) 0.5.degree.; (iii) 0.5-1.degree.; (iv) 1-2.degree.; (v) 2-4.degree.; (vi) 4-6.degree.; (vii) 6-8.degree.; (viii) 8-10.degree.; and (ix) >10.degree.

7. The sample plate of claim 1, wherein the diameter or depth of said recess is selected from the group consisting of: (i)<0.5 mm; (ii) 0.5-1.0 mm; (iii) 1.0-1.5 mm; (iv) 1.5-2.0 mm; (v) 2.0-2.5 mm; (vi) 2.5-3.0 mm; (vii) 3.0-3.5 mm; (viii) 3.5-4.0 mm; (ix) 4.0-4.5 mm; (x) 4.5-5.0 mm; (xi)<5.0 mm; and (xii) >5.0 mm.

8. The sample plate of claim 1, wherein in at least one sample well said base portion is segmented into a plurality of segments which are arranged at different heights relative to each other.

9. The sample plate of claim 1, wherein in at least one sample well, said sample well further comprises one or more baffles or dividers which separates or divides said base portion into at least a first region and a second region.

10. The sample plate of claim 9, wherein said one or more baffles or dividers attenuate or eliminate light reflected off one or more reagent beads located in said first region from impinging upon one or more reagent beads located in said second region.

11. The sample plate of claim 1, wherein said two or more recesses comprise a countersunk or enlarged portion for facilitating the insertion of a bead into one or more of said through holes or recesses.

12. The sample plate of claim 1, wherein said one or more sample wells comprises between 2 and 22 recesses.

13. The sample plate of claim 12, wherein said two or more recesses are arranged circumferentially around a central portion of said sample well.

14. The sample plate of claim 13, wherein said central portion comprises a central recess.

15. The sample plate of claim 14, wherein said central portion does not comprise a recess.

16. The sample plate of claim 13, wherein said plurality of recesses is arranged in a substantially symmetrical or regular manner.

17. The sample plate of claim 13, wherein said two or more recesses is arranged in a substantially asymmetrical or irregular manner.

18. The sample plate of claim 13, wherein said two or more recesses is arranged in a substantially linear manner.

19. The sample plate of claim 13, wherein said two or more recesses is arranged in a substantially curved manner.

20. The sample plate of claim 1, wherein said sample plate comprises sample wells arranged in an A×B format, wherein A and B are perpendicular axes, and the number of wells along said A axis can be greater than, less than, or equal to the number of wells along said B axis.

21. The sample plate of claim 20, wherein said number of wells along said A axis or B axis is at least 2.

22. The sample plate of claim 20, wherein said number of wells along said A axis or B axis is between 2 and 15.

23. The sample plate of claim 1, wherein one of said sample wells is connected to another sample well by a frangible region.

24. The sample plate of claim 1, wherein said sample plate comprises a base comprising a docking portion for securing said sample plate to a corresponding docking portion of a plate frame holder.

25. The sample plate of claim 1, further comprising a bead.

26. The sample plate of claim 25, wherein said bead is attached to a probe.

27. The sample plate of claim 26, wherein said probe is a nucleic acid, antibody, antibody fragment, protein, peptide, aptamer, or chemical compound.

28. A bead dispensing system comprising:
    (a) a plurality of beads;
    (b) a bead dispenser for dispensing at least some of said plurality of beads;
    (c) a sample plate comprising a sample well, wherein said sample well comprises a base portion, wherein said base portion comprises one or more recesses, wherein each of said one or more recesses has a dimension for a bead deposited in said well to be substantially retained or secured within said recess, and said bead forms a substantially fluid-tight circumferential seal with a wall of said base portion which defines said recess; and
    (d) a control system configured to control dispensing of said bead from said bead dispenser into said sample plate.

29. The bead dispensing system of claim 28, wherein said one or more recesses comprise a blind recess or an open through hole.

30. The bead dispensing system of claim 28, wherein said bead dispenser comprises: (i) a syringe body comprising an annular chamber surrounding a longitudinal bore, wherein said annular chamber is configured to channel a reagent bead within said annular chamber towards a chamber provided in said bore;
    (ii) a plunger provided within said longitudinal bore; and
    (iii) a barrel or nozzle; wherein said plunger is configured to dispense a bead of said plurality of beads from said chamber into said barrel or nozzle.

31. The bead dispensing system of claim 28, wherein said bead dispenser is configured to dispense the plurality of beads automatically.

32. A method of dispensing beads comprising:
(a) providing a bead dispenser comprising a bead;
(b) providing a sample plate comprising a sample well, wherein said sample well comprises a base portion; wherein said base portion comprises two or more recesses, wherein each of said two or more recesses has a dimension for a bead deposited in said well to be substantially retained or secured within said recess, and said bead forms a substantially fluid-tight circumferential seal with a wall of said base portion which defines said recess; and
(c) controlling the dispensing of said bead from said bead dispenser into said sample plate.

33. The method of claim 32, wherein said two or more recesses comprise a blind recess or an open through hole.

34. The method of claim 32, wherein said dispensing is performed automatically.

35. A kit for detecting an analyte comprising:
(a) a plurality of beads; and
(b) sample plate comprising a sample well, wherein said sample well comprises a base portion; wherein said base portion comprises one or more recesses, wherein each of said one or more recesses has a dimension for a bead deposited in said well to be substantially retained or secured within said recess, and said bead forms a substantially fluid-tight circumferential seal with a wall of said base portion which defines said recess.

36. The kit of claim 35, wherein said one or more recesses comprise a blind recess or an open through hole.

37. The kit of claim 35, wherein said plurality of beads comprise one or more probes.

38. The kit of claim 37, wherein said probe is a nucleic acid, antibody, antibody fragment, protein, peptide, aptamer, or chemical compound.

39. A method of detecting an analyte comprising:
(a) adding a sample to a sample plate comprising a sample well, wherein said sample well comprises a base portion; wherein said base portion comprises two or more recesses, wherein each of said two or more recesses has a dimension for a bead deposited in said well to be substantially retained or secured within said recess, wherein at least one of said one or more recesses contains a bead and said bead forms a substantially fluid-tight circumferential seal with a wall of said base portion which defines said recess, and wherein said bead comprises a probe; and
(b) detecting binding of an analyte in said sample with said probe.

40. The method of claim 39, wherein each of said two or more recesses comprises a blind recess and an open through hole.

41. The method of claim 39, wherein said sample plate comprises a plurality of probes and a plurality of analytes are detected.

42. The method of claim 39, wherein a plurality of samples is added to said sample plate.

43. A method of manufacturing a sample plate comprising:
(a) providing a sample plate comprising one or more sample wells each having a base portion; and
(b) forming two or more recesses in said one or more base portions, wherein each of said two or more recesses has a dimension and contains a bead deposited in said well, in use, to be substantially retained or secured within said recess, and said bead, in use, forms a substantially fluid-tight circumferential seal with a wall of said base portion which defines said recess.

44. The method of claim 43, wherein each of said two or more recesses comprises a blind recess or an open through hole.

* * * * *